(12) United States Patent
Rekik

(10) Patent No.: US 11,484,513 B2
(45) Date of Patent: Nov. 1, 2022

(54) SALBUTAMOL-CONTAINING OPHTHALMIC MEDICAMENT

(71) Applicant: Raouf Rekik, Tunis (TN)

(72) Inventor: Raouf Rekik, Tunis (TN)

( * ) Notice: Subject to any disclaimer, the term of this patent is extended or adjusted under 35 U.S.C. 154(b) by 0 days.

(21) Appl. No.: 16/313,425

(22) PCT Filed: Jun. 27, 2017

(86) PCT No.: PCT/IB2017/000779
§ 371 (c)(1),
(2) Date: Dec. 26, 2018

(87) PCT Pub. No.: WO2018/007864
PCT Pub. Date: Jan. 11, 2018

(65) Prior Publication Data
US 2019/0160027 A1 May 30, 2019

(30) Foreign Application Priority Data
Jun. 27, 2016 (TN) .................................. 2016/0259

(51) Int. Cl.
| | | |
|---|---|---|
| *A61K 31/137* | (2006.01) | |
| *A61K 31/198* | (2006.01) | |
| *A61K 31/403* | (2006.01) | |
| *A61K 31/585* | (2006.01) | |
| *A61P 27/06* | (2006.01) | |
| *A61K 9/00* | (2006.01) | |
| *A61K 38/00* | (2006.01) | |
| *A61K 45/06* | (2006.01) | |

(52) U.S. Cl.
CPC .......... *A61K 31/137* (2013.01); *A61K 31/198* (2013.01); *A61K 31/403* (2013.01); *A61K 31/585* (2013.01); *A61P 27/06* (2018.01); *A61K 9/0048* (2013.01); *A61K 38/005* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 3,985,897 A | | 10/1976 | Seidehamel |
| 5,192,780 A | * | 3/1993 | York ....................... A61K 31/44 514/357 |
| 6,569,903 B2 | * | 5/2003 | Honma ............... A61K 31/4704 514/649 |
| 7,015,210 B2 | * | 3/2006 | Aiken ....................... A61P 3/10 514/171 |
| 9,155,719 B2 | * | 10/2015 | Rekik ..................... A61P 43/00 |
| 2003/0158162 A1 | | 8/2003 | Aiken |

FOREIGN PATENT DOCUMENTS

| | | | | |
|---|---|---|---|---|
| EP | 1153614 | | 11/2001 | |
| EP | 2808010 A1 | * | 12/2014 | ........... A61K 31/137 |
| WO | 2006064283 | | 6/2006 | |
| WO | 2011068786 | | 6/2011 | |
| WO | 2011151685 | | 12/2011 | |
| WO | 2012073077 | | 6/2012 | |

OTHER PUBLICATIONS

Manaviat et al. "Prevalence of Dry Eye Syndrome and Diabetic Retinopathy in Type 2 Diabetic Patients". BMC Ophthalmology. 2008; 8:10. (Year: 2008).*
Yun et al. "Beta-Adrenergic Receptor Agonists Attenuate Pericyte Loss in Diabetic Retinas Through Akt Activation". FASEB J. 2018; 32:2324-2338. Published Online Dec. 2017. (Year: 2017).*
Von Lueder et al. "RAAS Inhibitors and Cardiovascular Protection in Large Scale Trials". Cardiovasc Drugs Ther. 2013; 27:171-179. (Year: 2013).*
Blumenfeld et al. "Beta-Adrenergic Receptor Blockage as a Therapeutic Approach for Suppressing the Renin-Angiotensin-Aldosterone System in Normotensive and Hypertensive Subjects". AJH. 1999; 12:451-459. (Year: 1999).*
Millar et al. "Investigation of the Mechanism of Beta 2-Agonist-Induced Activation of the Renin-Angiotensin System". Clin Sci (Lond). Apr. 1995; 88(4):433-437. Abstract Only. (Year: 1995).*
Bauer et al., "Benazepril, am angiotensin converting enzyme inhibitor: drug interaction with salbutamol and bronchial response to histamine in normal subjects", Br J Clin Pharmacol, 1997, 44: 573-575.

* cited by examiner

*Primary Examiner* — Leslie A. Royds Draper
(74) *Attorney, Agent, or Firm* — Duane Morris LLP; Gregory M. Lefkowitz; Brandon A. Chan

(57) ABSTRACT

The invention relates to a medicament, the active principle of which is Salbutamol. It can be applied to the prevention and/or treatment of eye diseases or disorders, especially of Ametropia (myopia, Presbyopia), hereditary dystrophies of the retina, glaucoma, cataract, Keratoconus, macular degeneration, diabetic retinopathy, orbital and ocular inflammation (optic neuritis, uveitis), vitreo retinal proliferation or fibrosis, conjunctivitis, dry eye and all the ophthalmic diseases or disorders including a decrease of visual function.

13 Claims, 26 Drawing Sheets

SALBUTAMOL-CONTAINING OPHTHALMIC MEDICAMENT

CROSS-REFERENCE TO RELATED APPLICATIONS

This application is a § 371 national stage entry of International Application No. PCT/IB2017/000779, filed Jun. 27, 2017, which claims priority to Tunisian Patent Application No. TN 2016/0259 filed Jun. 27, 2016, the entire contents of which are incorporated herein by reference.

FIELD OF THE INVENTION

The invention relates to compositions comprising at least Salbutamol or a pharmaceutically acceptable salt thereof for use as a protective ophthalmic medicament. In the context of this therapeutic use, the compositions of the invention may also comprise or consist essentially of or consist of Salbutamol or a pharmaceutically acceptable salt thereof, associated with one or several further active principle(s) selected from the group consisting of: beta 1 adrenergic blockers, alpha 2 adrenergic agonists, anhydrase carbonic inhibitors, angiotensin converting enzyme inhibitors, aldosterone receptor antagonist, N Acetyl DL Leucine, glucose, magnesium, potassium, nitric monoxide donors, steroidal anti inflammatory drugs, non steroidal anti inflammatory drugs, proteolytic enzyme, one of their pharmaceutically acceptable salts thereof, and mixtures thereof. Method of preventing and/or treating one or several ophthalmic disease(s) involving a deterioration of the eye and/or of the visual function are also disclosed using such compositions. The invention discloses, in particular, medications for the treatment of ophthalmic disease(s) selected from the group comprising: hereditary dystrophies of the retina, glaucoma, glaucoma neuropathy, age related macular degeneration, ametropia, dry eye, hereditary dystrophies of ocular inflammation, ocular inflammation, uveitis, orbital inflammation, cataract, allergic conjunctivitis, diabetic retinopathy, macular oedema, corneal oedema, keratoconus, proliferative vitreo retinopathy (fibrosis), peri-retinal fibrosis, central serious chorio retinopathy, vitreo retinal pathology, vitreo macular traction and vitreous hemorrhage. The invention also concerns compositions, kit-of-parts (products presented side-by-side that can be applied simultaneously, separately or at intervals) or kits, especially suitable for use in the methods of the present invention. According to a particular aspect, the protective ophthalmic compositions and medicament of the Invention can maintain or ameliorate the visual function such as visual acuity or visual field in the eye(s) of patients in need thereof.

BACKGROUND AND MECHANISMS OF ACTION OF THE INVENTION

The invention is related to the production of medicament(s), especially an eye protective medicament(s) (or drug) for prevention and/or treatment of ophthalmic conditions leading to eye damage which result in a vision loss (especially far and near visual acuity and visual field).

The compositions of the invention are based on and comprise at least one active principle which is Salbutamol (also commonly identified under the name Albuterol in the literature).

Salbutamol is a beta 2-adrenergic agonist. More particularly, Salbutamol is a selective beta 2-adrenergic agonist, and a short acting beta 2-adrenergic agonist.

According to the invention, Salbutamol can be associated with other active principles and, in particular N Acetyl DL Leucine and/or corticosteroids and/or non steroidal anti-inflammatory agent drugs and/or Aldosterone receptors antagonist and/or angiotensin converting enzyme inhibitors and/or alpha 2 adrenergic agonists and/or beta 1 blockers and/or tetracycline and/or anhydrase carbonic inhibitor (such as acetazolamide) and/or proteolytic enzymes (such as serrapeptase).

The invention especially aims at providing medicaments intended for the prevention and/or the treatment of ophthalmic disease or disorders, in particular so as to maintain or improve the visual function of patients suffering from:

Visual refractive disorders, especially presbyopia, hypermetropia, myopia and astigmatism.
Diabetic retinopathy
Macular oedema
Serious central chorio-retinopathy
Age related macular degeneration
Retinal vein occlusion
Retinal artery occlusion
Uveitis
Papillitis, optic neuritis
Proliferative vitreo retinopathy and fibrosis
Hereditary dystrophies of retina comprising for example, pigmentosa retinopathy or Stargardt's disease.
Glaucoma and Glaucoma neuropathy
Cataract
Corneal oedema
Keratoconus
Dry eye
Allergic blepharitis and conjunctivitis
Vitreo macular traction
Vitreous hemorrhage.

The compositions and medicaments according to the invention and disclosed herein are not limited to the above-mentioned uses. They can be used efficiently in preventing or slowing down, or even stopping, the age-related decrease in visual acuity or visual field or both at the same time, especially in an aged subject. As detailed herein on the basis of the experiments provided in the Examples section, administration of Salbutamol to patients via the systemic route (especially in the oral or injectable form) or the topical route (especially in the form of eye drops, an ointment or cream or intraocular injection) imparts visual acuity, contrast vision, color vision but also visual field improvements in treated patients.

Salbutamol (also commonly known as Albuterol in the literature) is a molecule having the following chemical structure and formula:

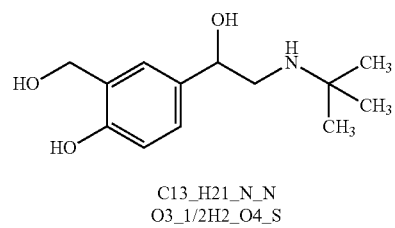 [SMILES: CC(C)(C)NCC(O)c1ccc(O)c(CO)c1]

C13_H21_N_N
O3_1/2H2_O4_S

Other beta 2 adrenergic agonists are known in the art: SalmeterolXinafoate, Terbutaline sulfate, Pirbuterolmetaproterol, Formoterol, Bitolterol, Arfomoterol, Buphenine, Clunbuterol, Isoltarine, Levosalbutamol, Orciprenaline, Procaterol, Ritodrine.

Beta 2 adrenergic agonists act mainly on the smooth muscle of the vasculature, bronchial, intestine, uterus and the eye. Beta 2 adrenergic agonists are used largely for treating asthma and are widely used and proven to be well tolerated and safe.

Although Salbutamol has a favorable effect on asthma, its potential for ophthalmic applications was unknown before the present invention was made.

The potential of Salbutamol within an association involving other active principle(s) as described in the present application, especially but not only active principles acting a inhibitors of the renin-angiotensin-aldosterone system (RAAS), optionally with further active ingredients, for ophthalmic applications was also unknown before the present invention was made.

As disclosed herein in the Examples, observations based on real essays were made in patients having, in particular, a glaucomatous neuropathy or glaucoma, a hereditary dystrophy of the retina (for example, Pigmentosa retinopathy or Stargardt's disease), macular degeneration, diabetic retinopathy, Uveitis, refractive disorders as myopia, Hypermetropia, Presbyopia and age-related physiologic loss of vision, cataract, corneal oedema, Keratoconus, proliferative retinopathy and central serious chorio retinopathy. These diseases can involve severe impairment, in the course of several months, or years. No perfect cures are available to date. So there remains a continuous need for improvement in treatments aimed at preventing or treating such invalidating diseases, and/or at least maintaining or ameliorating the visual function of patients having such diseases or their symptoms.

The present invention fulfills this need and provides compositions, especially ophthalmic compositions that showed to act as protective ophthalmic medicaments, as detailed herein.

The invention and its achievements are evidenced by the summary of the invention, detailed description, clinical observations and the claims.

Mechanisms of Action 1. cAMP Production: Role in Physiology

Salbutamol is a beta 2 adrenergic agonist and it stimulates beta 2 receptors. Binding of Albuterol to beta 2 receptors in the lungs results in relaxation of bronchial smooth muscles. It is believed that Salbutamol increase cAMP production by activating adenylate-cyclase and the action of Salbutamol is mediated by cAMP-dependant protein kinase A, which inhibits the phosphorilation of myosin and lowers intracellular calcium concentrations. A lowered intracellular concentration leads to a smooth muscle relaxation and broncho dilatation. In addition to broncho-dilatation, Salbutamol inhibits the release of a broncho constricting agents from mast cells, inhibits micro-vascular leakage.

Na+/K+ ATPase

Na+/K+ ATPase (sodium—potassium adenosine triphosphate, also known as the Na+/K+ pump or sodium potassium pump) is an enzyme found in the plasma membrane of all animal cells. The Na+/K+ ATPase enzyme is a pump that pumps sodium out of cells while pumping potassium into cells, both against their concentration gradients. This pumping is active (it uses energy from ATP) and is important for cell physiology.

Mechanism

The pump, after binding 3 intracellular Na+ ions,
ATP is hydrolyzed, leading to phosphorylation of the pump with subsequent relax of ADP,
A conformational change in the pump exposes the Na+ to the outside. The phosphorylated form of the pump has a low affinity for Na+ ions, so they are released,
The pump binds 2 extracellular K+ ions. This causes the dephosphorylation of the pump reverting it to its previous conformational state, transporting the K+ ions into the cell.

Function

The function of Na+/K+ ATPase:

It helps maintain resting potential effect transport, and regulates cellular volume. In most animal cells, the Na+/K+ ATPase can be responsible for about 20% of the cell's energy expenditure. For nervous, the Na+/K+ ATPase can be responsible for up to 2/3 cell's energy expenditure.

a. Transport of Energy Sources:

Export of sodium from the cell provides the driving force for several secondary active transporters membrane proteins, which import glucose, amino acids and other nutriments into the cell by use of the sodium gradient that is a source of energy for the cell.

b. Controlling Cell Volume:

Failure of the Na+/K+ pumps can result in swelling of the cell. A cell's osmolarity is the sum of the concentration of the various conspecies and many proteins. When this is higher than the osmolarity outside of the cell, water flows into the cell through osmosis. This can cause the cell to swell up and lyse. The Na+/K+ pumps help to maintain the right concentrations of ions furthermore, when the cell begins to swell, this automatically activates the Na+/K+ pump.

c. Calcium

Since the carrier enzyme (Na+_Ca2+ tranlocator) uses the Na+ gradient generated by the Na+/K+ pump to remove Ca2+ from intracellular space, slowing down of the Na+/K+ pump results in a permanently elevated Ca2+ level.

d. Regulation

The Na+/K+ ATPase is up regulated by cAMP. The substance causing an increase in cAMP, up regulates the Na+/K+ ATPase. In contrast, substances causing a decrease in cAMP down regulate the Na+/K+ ATPase.

2. cAMP: Role in Pathology:

It is suggested that activation of cAMP inhibits TNF Alpha.

Tumor Necrosis Factor Alpha (TNFα or TNF Alpha Herein):

Is a cell signaling protein (cytokin) involved in systemic inflammation. It is produced chiefly by macrophage, although it can be produced by many other cell types such as CD4+ lymphocytes, NK cells, neutrophils, mast cells, exinophils and neurons (retinal). TNF is able to induce apoptic cell death, inflammation and inhibit tumorogenesis.

Tumor Necrosis Factor α is a potent stimulator of angiogenesis. It can induce the expression of vascular cell adhesion molecule_1 (VCAM_1) on the surface of endothelial cells.

The soluble form of VCAM_1 has recently been demonstrated to function as an angiogenic mediator. TNFα acts by inducing the release of factors such as VEGF and FGF.

Stimulation of beta 2 adrenergic receptors inhibits the release of Tumor Necrosis Factor. Alpha cAMP elevating agents (β2 adrenergic such as SALBUTAMOL, prostaglandin) reduce the plasma TNF level and then reduce VEGF.

Through TNFα inhibition, beta 2 adrenergic agonist reduce the activity of matrix metalloproteinase.

TNFα stimulates activation of MMP2 (matrix metalloproteinase 2) and MMP9 (matrix metalloproteinase 9).

This explain why beta 2 adrenergic agonists reduce the activity of matrix metalloproteinase improving pathologic conditions.

In fact, the MMPs play an important role in tissue remodeling associated with various physiological or pathological processes such as morphogenesis, tissue repair, fibrosis, blood clot, artrosis, arthritis, cancer invasion and metastasis, rumatoid arthritis, ulcers, brain injuries and neuro inflammatory disease, fibrosis (cirrhosis, fibrotic lung disease) osteosclerosis, atherosclerosis and multiples sclerosis. Weakening of matrix, as in dilated cardiomyopathy, aortic aneurysm. Angiogenesis, apoptosis, diabetes and hypertension.

3. So in Conclusion, Salbutamol Through cAMP has a Double Role:
   1) Physiologic role with energy production and homeostasis improving visual function.
   2) In pathology through TNFα and MMPs (matrix metalloproteinases) inhibition: improves apoptosis, inflammation, angiogenesis, fibrogenesis and excitoxicity.

Localization of beta adrenergic receptors in rabbit eye, using in vitro autoradiography showed that the majority of beta-adrenergic receptors, detectable by autoradiography, were of the beta 2 type in the eye and were widely distributed in the ocular tissues (conjunctiva, cornea, ciliary processes, lens, retina choroid and extra ocular muscles). It had been proven that beta 1 adrenergic receptors are located in retina vasculature and beta 2 adrenergic receptors are distributed in retina Muller cells.

Beta Adrenergic Receptor in Ageing in Pathology

G protein-coupled receptors play a key role in cellular communication, allowing human cells to sense external cues or to talk each other through hormones or neurotransmitters.

Beta adrenergic receptors (BARs) mediate physiological responses to catecholamines. There are three receptors subtypes in the BAR family: Beta1AR is found at its highest levels in the heart, Beta2AR is distributed extensively throughout the body and the Beat3AR is mainly expressed in the white and brown adipose tissue.

Beta2AR is coupled to the G protein and resulted in activation of adenyl cyclase, which is turn catalyzes the conversion of adenosine triphosphate to cyclic AMP.

Understanding ageing: ageing is a complex process characterized by a gradual decline in organ functional reserves which eventually reduce the ability to maintain homeostasis. Several theories of ageing have been proposed: the somatic mutation theory relates to the failure of DNA repair, the free radical theory related to the failure of defenses against reactive oxygen species, the auto immune theory proposes that the immune system eventually fails to distinguish self from non-self antigens. Other researchers relate to the deleterious effects of toxic chemicals.

In this disclosure it is presented an updated exposition of the current knowledge in the relationship between ageing and BARs. There is a potential reciprocal regulation of ageing and BARs in various districts and particularly in the eye, providing both molecular and clinical implication for the use of known pharmaceutical compounds such as BAR agonist agents in elderly.

Experimental findings indicate an age-associated decrease in catecholamine responsiveness in the elderly. The age related deterioration in Beta2AR function and subsequent cAMP reduced generation is suggested. Concerning the molecular mechanisms, many theories have been proposed:
   A decreased receptor density,
   Less efficient coupling to adenylate cyclase,
   Impaired generation of cAMP,
   Current evidence suggests that the enhanced matrix metalloproteinase activity (MMPs activity) which causes cleavage of the extracellular domain of membrane receptors such as the insulin receptor and the membrane integrin CD18, seems to effect also Beta2ARs that control vasodilatation, the peripheral vascular resistance and the blood pressure levels.

Beta 1 adrenergic blockers, angiotensin receptors agonists, converting enzyme inhibitors (such as Ramiprilat), non steroidal anti inflammatory agents, anti-renin, anti-aldosterone (such as eplerenone), carbonic anhydrase inhibitors, N Acetyl DL Leucine, vitamin B9 (folic acid), vitamin C, tetracycline, inhibit MMP (matrix metalloproteinase) and so improve Beta2 Adrenergic receptors and Beta2 Adrenergic agonist activity (Salbutamol).

However, there is not a single cellular or molecular factor that can fully explain the age-related decline in Beta2 adrenergic function. The latter seems to be the cause of energy decline, homeostasis imbalance, an increase of TNFα (TNFalpha) secretion, MMP activation and finally an elevation in basal levels of circulating catecholamines inducing an increased alpha1 and beta1 adrenergic function generating apoptosis, inflammation; fibrosis and intraocular pressure elevation. It had been suggested that age-related alteration may be due to the cleavage of the extracellular domain of membrane receptors (Beta2 adrenergic receptor and insulin receptor).

Beta2AR Knockout Mice Exhibit a Diabetic Retinopathy Phenotype.

There is considerable evidence for a functional link between BARs and insulin receptor signaling pathway in retina. Furthermore, it is hypothesized that this link may contribute to lesion similar to diabetic retinopathy. Loss of Beta2 adrenergic input resulted in an increase in TNFα (TNFalpha), a key inhibitor of insulin receptor signaling. It is postulated that aspects of the diabetic retinopathy phenotype might be triggered by loss of β2AR signaling. However, MMPs probably causes cleavage of insulin receptor.

The role of Beta2AR in inflammation and allergy: beta 2 adrenergic receptor seems to play an active role in allergy and inflammation. The stimulation of Beta2AR inhibits release of pro inflammatory mediators.

Salbutamol is a selective beta2 adrenergic, and as such this molecule is distinct from selective beta1 adrenergics, selective beta3 adrenergics or non-selective beta adrenergics, the latter of which being both beta1 and beta2 adrenergics. Salbutamol is also distinct from alpha adrenergics. All these agents have different modes of action and involve different biological pathways. Treating chronic ophthalmic diseases or disorders having a high incidence in the general population, and severe consequences, such as diabetic retinopathy, age-related macular degenerescence, uveitis, glaucoma is generally achieved in the art using beta blockers. Beta blockers block beta adrenergic receptors. They do not activate them.

The art also tends to propose the use of inhibitors of the renin-angiotensin-aldosterone system (RAAS), such as, for example, beta blockers, anti-renins, inhibitors of angiotensin converting enzyme (ACEI), antagonists of angiotensin 2, anti-aldosterones.

Beta blockers are known to have anti-inflammatory properties, anti-angiogenic properties and may be used in uveitis, diabetic retinopathy and central serous chorioretinopathy (CSCR) treatment.

As of today, using in this context Salbutamol, a beta adrenergic agonist, goes against prior art indications and recommendations. It follows from the above that the skilled person would not be directed towards using in association beta blockers (which are anti-RAAS agents) with RAAS inhibitors (such as ramiprilat or eplerenone). In particular, the present disclosure proves the potential of Salbutamol within an association involving other active principle(s) as described in the present application, especially but not only active principles acting a inhibitors of the renin-angiotensin-aldosterone system (RAAS), optionally with further active ingredients, for ophthalmic applications, as described herein.

The invention will be illustrated further by the description of clinical Examples which, of course, are not limiting in nature.

SUMMARY OF THE INVENTION

A composition comprising at least Salbutamol or a pharmaceutically acceptable salt thereof for use as a protective ophthalmic medicament is provided by the present invention, Composition for use of the present invention can comprise or consist essentially of or consist of Salbutamol or a pharmaceutically acceptable salt thereof and one or several further active principle(s) selected from the group consisting of: beta 1 adrenergic blockers, alpha 2 adrenergic agonists, anhydrase carbonic inhibitors, angiotensin converting enzyme inhibitors, aldosterone receptor antagonist, N Acetyl DL Leucine, glucose, magnesium, potassium, nitric monoxide donors, steroidal anti inflammatory drugs, non steroidal anti inflammatory drugs, proteolytic enzyme, one of their pharmaceutically acceptable salts thereof, and mixtures thereof.

According to a particular embodiment, a composition for use as a protective ophthalmic medicament of the invention consists essentially of or consists of Salbutamol or a pharmaceutically acceptable salt thereof.

Conversely, in another aspect, the composition for use of the invention can associate Salbutamol or a pharmaceutically acceptable salt thereof with other active principles as described herein, in particular active principles acting as inhibitors of the renin-angiotensin-aldosterone system (RAAS), as described herein, and optionally further active principles, as described herein.

According to particular embodiment, the compositions for use of the present invention can comprise or consists essentially of or consists of:
  Salbutamol, N Acetyl DL Leucine, magnesium, potassium and nitric monoxide donor(s), or
  Salbutamol, angiotensin converting enzyme inhibitor(s), aldosterone receptor antagonist(s), N Acetyl DL Leucine, magnesium, and proteolytic enzyme, or
  Salbutamol, angiotensin converting enzyme inhibitor(s), aldosterone receptor antagonist(s), N Acetyl DL Leucine, or
  Salbutamol, angiotensin converting enzyme inhibitor(s) and aldosterone receptor antagonist(s).

According to another aspect, the compositions described in the above paragraph can also include other active principles as disclosed herein, in all combinations thereof.

According to the invention, the angiotensin converting enzyme inhibitors or active metabolites thereof, the aldosterone receptor antagonists, the nitric monoxide donors, the steroidal anti inflammatory drugs, the non steroidal anti inflammatory drugs, the proteolytic enzymes can be as disclosed in the detailed description herein.

According to particular embodiment, the composition for use of the present invention can comprise or consists essentially of or consists of:
  Salbutamol, ramiprilate, eplerenone and N Acetyl DL Leucine, or
  Salbutamol, ramiprilate and eplerenone.

It is observed that ramiprilate and eplerenone are active principles acting as inhibitors of the renin-angiotensin-aldosterone system (RAAS). The invention encompass the use of such compounds, possibly in association with further active ingredients as disclosed herein.

In another aspect of the invention, the composition for use can further comprise pharmaceutically acceptable additive(s), dilent(s) or vehicle(s) or carrier(s).

In another aspect, the invention relates to the use of the compositions of the invention for use as a protective ophthalmic medicament in a method of preventing and/or treating one or several ophthalmic disease(s) involving a deterioration of the eye and/or of the visual function, wherein said ophthalmic disease(s) is(are) selected from the group comprising: hereditary dystrophies of the retina, glaucoma, glaucoma neuropathy, age related macular degeneration, ametropia, dry eye, hereditary dystrophies of ocular inflammation, ocular inflammation, uveitis, orbital inflammation, cataract, allergic conjunctivitis, diabetic retinopathy, macular oedema, corneal oedema, keratoconus, proliferative vitreo retinopathy (fibrosis), peri-retinal fibrosis, central serious chorio retinopathy, vitreo retinal pathology, vitreo macular traction and vitreous hemorrhage.

According to particular embodiments, the ophthalmic disease(s) can be as disclosed in the detailed description herein.

The compositions of the invention, as described herein can be administered orally, parentally, intravenously, intravascularly, intramuscularly, transdermally, or topically. In another embodiment, they can be administered topically to the eye, especially through eye drops or intraocular injection or intravitreal injection. In another embodiment, they can be in the form of a solution, a lotion, drops, a cream or an ointment. In another embodiment, they can be in the form of an ophthalmic solution or eye drops, or be administered as eye drops into the eye(s).

According to particular embodiments, the composition for use according to the invention encompass administration of the following active principles as follows:
  Salbutamol is administered topically in a concentration ranging from 0.05 to 0.2% (w/v), or ranging from 0.05 to 0.1% (w/v), in particular at a concentration of 0.1% (w/v), and/or
  Ramiprilate is administered topically in a concentration ranging from 0.5 to 5% (w/v), or ranging from 0.5 to 3% (w/v), or ranging from 0.5 to 2% (w/v), for example at 0.5%, 1% or 2% (w/v), and/or
  eplerenone is administered topically in a concentration ranging from 0.5 to 5% (w/v), or ranging from 0.5 to 3% (w/v), or ranging from 1 to 2% (w/v), for example at 0.5%, 1% or 2% (w/v), and/or
  N Acetyl DL Leucine is administered topically in a concentration ranging from 0.5 to 5% (w/v), or ranging from 0.5 to 3% (w/v), or ranging from 1 to 2% (w/v), for example at 0.5%, 1% or 2% (w/v).

According to particular aspects, the active principle(s) can be administered once or twice or three times, and up to four times a day, and/or administered during 1, 2 or 3 months, or more. The active principle(s) as disclosed in any one of the embodiments herein can be found within a single composition or in separate compositions, and/or can be administered simultaneously, sequentially or separately to a subject in need thereof.

According to a particular embodiment, wherein several active principles found in one or several compositions are administered sequentially over time to a subject in need thereof, the following scheme may be followed:

Salbutamol is administered topically once or twice or three times, and up to four times a day, during 1, 2 or 3 months, or more, and then Salbutamol, ramiprilate, eplerenone and N Acetyl DL Leucine are simultaneously, sequentially or separately administered topically once or twice or three times, and up to four times a day, during 1, 2 or 3 months, or more, or Salbutamol, ramiprilate and eplerenone are simultaneously, sequentially or separately administered topically once or twice or three times, and up to four times a day, during 1, 2 or 3 months, or more.

The invention also relates to the use of the compositions described herein for maintaining or improving the visual function, in particular the visual acuity and/or visual field, of a subject in need of such treatment.

The invention further relates to a method for preventing and/or treating one or several ophthalmic disease(s) or disorder(s) involving a deterioration of the eye and/or of the visual function, comprising administering to a subject in need thereof a composition comprising at least Salbutamol or a pharmaceutically acceptable salt thereof. According to particular embodiments described herein, the method of the invention can further comprises administering one or several active principle(s) or composition(s) as described in any one of the embodiments of the present description, wherein said several active principles are administered simultaneously, sequentially or separately, within a single or several separate composition(s).

Within a method of treatment as described herein, the compositions, the administration routes, the formulation of the compositions, the dosages, concentrations, posologies, duration of the treatment or administration schedule (including when separate compositions are administered), can be as described above and herein.

The invention further relates to compositions characterized in that it comprises or consists essentially of, or consists of:

Salbutamolv or a pharmaceutically acceptable salt thereof, and

One or several active principle(s) selected from the group consisting of: beta 1 adrenergic blockers, alpha 2 adrenergic agonists, anhydrase carbonic inhibitors, angiotensin converting enzyme inhibitors, aldosterone receptor antagonist, N Acetyl DL Leucine, glucose, magnesium, potassium, nitric monoxide donors, steroidal anti inflammatory drugs, non steroidal anti inflammatory drugs, proteolytic enzyme, one of their pharmaceutically acceptable salts thereof, and mixtures thereof, and Optionally, pharmaceutically acceptable additive(s), diluent(s) or vehicle(s) or carrier(s).

According to a particular embodiment, the compositions can comprise or consist essentially of or consist of:

Salbutamol, ramiprilate, eplerenone and N Acetyl DL Leucine, or

Salbutamol, ramiprilate and eplerenone.

According to particular aspects, the features described herein regarding the compositions for use, can also apply to compositions per se.

The invention also relates to a kit of parts of a first active principle that is Salbutamol or a pharmaceutically acceptable salt thereof, with one or more active principle(s) as herein, wherein said active principles are capable of jointly preventing and/or treating of one or several diseases as defined herein, and/or jointly maintaining or improving the visual function, are found in admixture or separately.

The invention also relates to a kit comprising or consisting essentially of or consisting of:

At least two active principles as defined herein, and

Optionally, instructions for using said kit, wherein said active principles are associated in a same composition or wherein at least two or more of these active principles are in separate compositions.

In another aspect, the products described herein can be used as a protective ophthalmic medicament, especially for a treatment described according to any embodiment of the present disclosure.

The invention also relates to the use of a composition, or a kit-of-parts or a kit according to the present disclosure, in the manufacture of a medicament intended for the any of the therapeutic uses defined herein. In a particular embodiment, the invention relates to the use of Salbutamol or a pharmaceutically acceptable salt thereof, in the manufacture of a protective ophthalmic medicament as disclosed herein.

DETAILED DESCRIPTION

Figure 1:
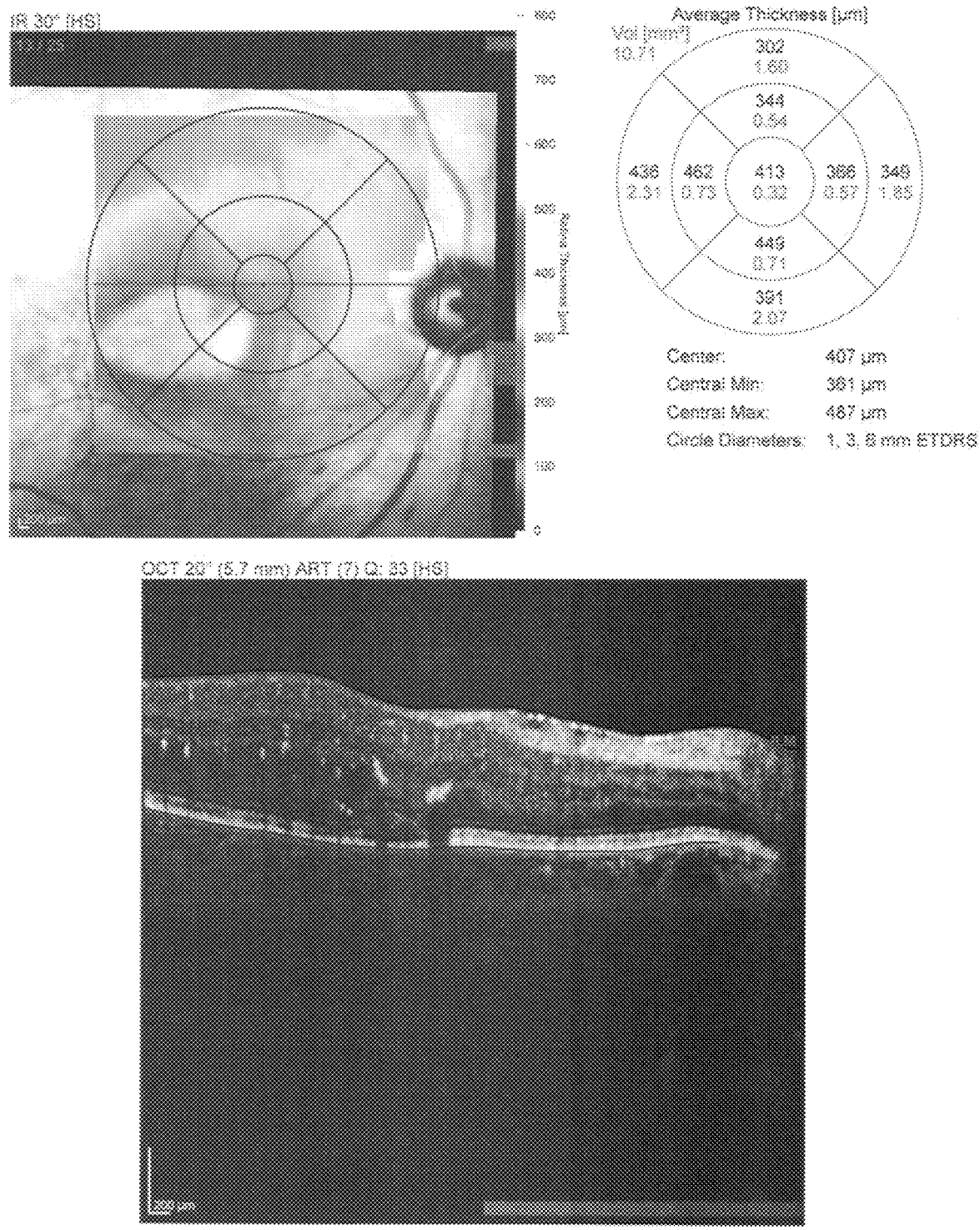
FIG. 1 is an optical coherence tomography scan (OCT) of patient B.Z., who has diabetic retinopathy, before treatment.

Unless otherwise indicated, each embodiment disclosed herein is applicable independently of and/or in combination with any one or several of the other described embodiments.

The invention relates, in particular, to the following embodiments:

Item 1. β2 adrenergic agonist for its use in preventing or treating several ophthalmic diseases in an animal in need, comprising a deterioration of the eye, said condition being chosen from
  Hereditary dystrophies of the retina
  Glaucoma Neuropathy
  Age related macular degeneration
  Ametropia; presbyopia
  Dry eye
  Ocular inflammation, uveitis
  Cataract
  Diabetic Retinopathy
  Macular Oedema
  Keratoconus
  Proliferative vitreo retinopathy (fibrosis)
  Central serious chorio retinopathy
  Vitreo macular traction
  Vitreous hemorrhage
said β2 adrenergic agonist being Salbutamol or a pharmaceutically acceptable salt thereof.

Item 2. β2 adrenergic agonist according Item 1., characterized in That said medicament comprises a pharmaceutically acceptable carrier for the administration of said medicament in oral, parenteral, intravascular, intramuscular, transdermal, intravitreous or topical form, Item 3. β2 adrenergic agonist according to either Item 1 or Item 2, characterized in that said medicament is for topical administration (eye drops, intraocular and intravitreal injection)

Item 4. β2 adrenergic, agonist according to any one of the preceding Items, characterized in that said medicament is an eye drops.

Item 5. β2 adrenergic agonist according to Items 1 to 4, characterized in that said medicament is for use in the hereditary dystrophies of the retina (Pigmentosa retinitis, Stargardt's disease)

Item 5. β2 adrenergic agonist according to Items 1 to 4, characterized in that said medicament is for use in Glaucoma neuropathy or Glaucoma.

Item 6. β2 adrenergic agonist according to Items 1 to 4, characterized in that said medicament is for use in age related macular degeneration.

Item 7. β2 adrenergic agonist according to Reins 1 to 4, characterized in that said medicament is for use in diabetic retinopathy.

Item 8. β2 adrenergic agonist according to Items 1 to 4, characterized in that said medicament is for use in macular Oedema.

Item 9. β2 adrenergic agonist according to Items 1 to 4, characterized in that said medicament is for use in Ametropia (Presbyopia, Myopia, Hypermetropia).

Item 10. β2 adrenergic agonist according to Items 1 to 4, characterized in that said medicament is for use in the hereditary dystrophies of ocular inflammation (Uveitis) Orbital inflammation.

Item 11. β2 adrenergic agonist according to Items 1 to 4, characterized in that said medicament is for use in dry eye.

Item 12. β2 adrenergic agonist according to Items 1 to 4, characterized in that said medicament is for use in cataract.

Item 13. β2 adrenergic agonist according to Items 1 to 4, characterized in that said medicament is for use in allergic conjunctivitis.

Item 14. β2 adrenergic agonist according to Items 1 to 4, characterized in that said medicament is for use in corneal oedema.

Item 15. β2 adrenergic agonist according to Items 1 to 4, characterized in that said medicament is for use in Keratoconus.

Item 16. β2 adrenergic agonist according to Items 1 to 4, characterized in that said medicament is for use in vitreo macular traction in order to trigger a vitreolysis in vitreo retinal pathology.

Item 17. β2 adrenergic agonist according to Items 1 to 4, characterized in that said medicament is for use in central serious chorio retinopathy, Item 18. β2 adrenergic agonist according to Items 1 to 4, characterized in that said medicament is for use in pen-retinal fibrosis.

Item 19. β2 adrenergic agonist according to Items 1 to 4, characterized in that said medicament is for use in vitreal hemorrhage.

Item 20. β2 adrenergic agonist according to any one of the preceding claims, characterized in that said medicament is for use in maintaining or improving visual acuity and visual field.

Item 21. Medicament comprising a β2 adrenergic agonist, said β2 adrenergic agonist being Salbutamol or a pharmaceutically acceptable salt thereof for its use as a protective ophthalmic medicament.

Item 22. Use of a β2 adrenergic agonist, said β2 adrenergic agonist being Salbutamol, or a pharmaceutically acceptable salt thereof, in the manufacture of a protective ophthalmic medicament as defined in any one of Items 1 to 20.

Item 23. A composition, characterized in that it comprises:
  Salbutamol
  One or several active principle (s) chosen among β1 blocker, anhydrase carbonic inhibitor, angiotensin converting enzyme inhibitor (Ramiprilat), aldosterone receptor antagonist (eplerenone), N Acetyl DL Leucine, Magnesium, potassium, nitric monoxide donor (vitamin C, vitamin B9), steroidal or non steroidal anti inflammatory drugs and proteolytic enzyme (serrapeptase).
  A pharmaceutically acceptable vehicle.

Item 24. The composition comprising Salbutamol, Eplerenone, Ramiprilat, N Acetyl DL Leucine and non steroidal anti inflammatory drug for use in the treatment of diabetic retinopathy, age related macular degeneration, uveitis, macular oedema and serious central chorioretinopathy.

Item 25. The composition comprising Salbutamol, N Acetyl DL Leucine, Magnesium and potassium for presbyopia.

Item 26. Medicament comprising these compositions for its use as a protective ophthalmic product.

The invention more particularly relates to a composition comprising at least Salbutamol or a pharmaceutically acceptable salt thereof for use as a protective ophthalmic medicament.

By "protective ophthalmic medicament", it is meant that the composition can be used in therapy that prevents, retards or reverses physical or functional damages associated with ophthalmic disease(s) or disorder(s) or their symptoms, as described herein.

As used herein, a "composition" refers to a product that may consists in a combination or union of several things; a combination, aggregate or mixture. Composition can also have the meaning of "combination", such as used in chemistry, or in general terms "assemblage". Accordingly, the expression "composition" used herein encompass both a mixture in which components are mixed together, or a combination of components that are presented side by side and can therefore be administered or applied simultaneously, separately or at intervals to a subject's body. A joint effect can however be attained through the combined product.

When the composition described herein encompass only the active principle that is Salbutamol or a pharmaceutically acceptable salt thereof, it will be understood that the term Salbutamol can be substituted to "composition", which is used herein for coherence and reading facility.

According to a particular embodiment, the composition comprises or consists essentially of or consists of Salbutamol or a pharmaceutically acceptable salt thereof and one or several further active principle(s) selected from the group consisting of: beta 1 adrenergic blockers, alpha 2 adrenergic agonists, anhydrase carbonic inhibitors, angiotensin converting enzyme inhibitors (such as Ramiprilat), aldosterone receptor antagonist (such as eplerenone), N Acetyl DL Leucine, glucose, magnesium, potassium, nitric monoxide donors (such as vitamin C, vitamin B9), steroidal anti inflammatory drugs, non steroidal anti inflammatory drugs, proteolytic enzyme (such as serrapeptase), one of their pharmaceutically acceptable salts thereof, and mixtures thereof.

By "beta-blocking agent" (or beta-adrenergic antagonist agent) it is meant herein a drug which blocks the action of epinephrine (adrenaline) and/or norepinephrine (noradrenaline) in a human and an animal body. These compounds are used notably to lower intraocular tension and/or to reduce eye's aqueous humor secretions. By "beta 1 adrenergic blocker", it is meant a beta-blocking agent that is an antagonist of the beta 1 adrenergic receptors. Known beta-blocking agents include timolol, sotalol, propranolol, penbutolol, nadolol, metoprolol, labetalol, esmolol, carteolol, bisoprolol, betaxolol, atenolol, acebutolol, levobunolol, metipranolol.

By "alpha 2 adrenergic agonists", it is meant a drug which has effects similar to, or the same as, epinephrine (adrenaline) or which is susceptible to epinephrine, or similar substances, such as biological receptors. Alpha 2 agonists are able to inhibit adenyl cyclase activity in a human and an animal body and are used notably as antihypertensives, sedatives, to reduce eye's aqueous humor secretions and to facilitate aqueous humor outflow via the uveoscleral route. Examples of alpha 2 agonists include brimonidine, aprachlonidine and clonidine.

Anhydrase carbonic inhibitors are a class of pharmaceuticals that suppress the activity of carbonic anhydrase. An example of "anhydrase carbonic inhibitor" is acetazolamide. Further examples of "anhydrase carbonic inhibitor" encompass methazolamide, dorzolamide or brinzolamide.

"ACE inhibitors", as used herein, is the abbreviation for angiotensin converting enzymes inhibitors, which block the conversion of angiotensin I to angiotensin II. ACE inhibitors also dilate blood vessels. They are known for use in patients with hypertension and congestive heart failure. ACE inhibitors, as described herein, encompass fosinopril, ramipril, captopril, trandolapril, moexipril, lisinopril, quinapril, enalapril, perindopril, benazepril and mixtures thereof, as well as their active metabolites, as further detailed hereafter.

According to a particular and preferred embodiment, active metabolites of said angiotensin converting enzyme inhibitor are selected from the group consisting of: fosinoprilate, trandolaprilate, moexiprilate, ramiprilate, quinaprilate, enalaprilate, perindoprilate and benazeprilate, and mixtures thereof.

According to a particular embodiment, the ACEI is Ramipril or Ramiprilate.

Ramprilate, which is the result of the deesterification of rampirill, has the formula:

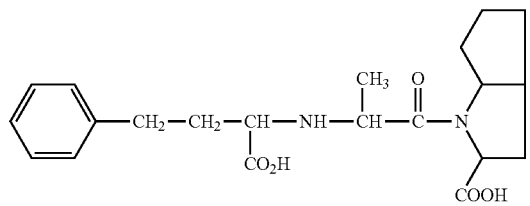 [SMILES: CC(NC(CCc1ccccc1)C(=O)O)C(=O)N1C(C(=O)O)CC2CCCC21]

Without doubt Ramipril and Ramiprilate intervene in the mechanism of action of angiotensin converting enzyme inhibitors (ACEI) in the measure where they act to prevent the transformation of angiotensin I to angiotensin II, which are vasoconstrictors and degrade brandykinins, which are vasodialators. These angiotensin converting enzyme inhibitors thus leads to vasodialation that has an effect also on the arteries and veins and is known as mixed vasodialators.

Aldosterone receptor antagonists (also called an antimineralocorticoid, MCRA, and sometimes MRA) are a class of drugs which block the effects of aldosterone. Aldosterone is the main mineralocorticoid hormone in the body and is produced in the adrenal cortex of the adrenal gland. Aldosterone increases sodium reabsorption by the kidneys, salivary glands, sweat glands and colon. At the same time, it increases the excretion of hydrogen and potassium ions. By blocking the effects of aldosterone, aldosterone receptor antagonists block the reabsorption of sodium, which encourages water loss. Consequently, this leads to a decrease in blood pressure and a reduction in fluid around the heart. Aldosterone receptor antagonists may be used in the treatment of high blood pressure or heart failure. They also have a weak diuretic action. Known examples of "aldosterone receptor antagonists" include, spironolactone, eplerenone canrenone and potassium canrenoate or finerenone. Some drugs also have antimineralocorticoid effects secondary to their main mechanism of actions. Examples include progesterone, drospirenone, gestodene, and benidipine. All these compounds are encompassed within particular embodiments of the present invention. According of a particular embodiment, the "aldosterone receptor antagonist" is eplerenone.

The N-acetyl-DL-leucine ($C_8H_{15}NO_3$) is a small molecule, with a relatively simple chemical structure. This optically inactive product is the result of N-acetylation of α-amino-isocaproic acid ($C_6H_{13}NO_2$), the L isomer of which, leucine, is a widespread natural α-amino acid.

Leucine:

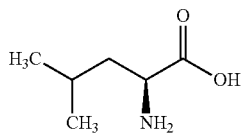

Conversely, the N-acetyl-DL-leucine has the following formula:

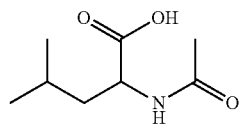

The effect of N-acetyl-DL-leucine on experimental vertigo in mice was discovered in 1957. Since this date, this compound is used successfully in human clinical medicine as a symptomatic medicament in vertigo states. The IN-acetyl-DL-leucine is widely prescribed by the doctors, well known from the pharmacists under the name Tanganil® (Pierre Fabre Medicament), and its efficiency is appreciated from many patients suffering from vertigo.

Pharmaceutically acceptable salts of magnesium and/or potassium that re encompassed within the present invention include for example potassium chloride and magnesium chloride, respectively.

Nitric monoxide (NO) donors are pharmacologically active substances that release NO in vivo or in vitro. Examples of nitric monoxide donors encompass vitamin C or vitamin B9 (folic acid), or mixtures thereof, which are accordingly disclosed herein as suitable for implementing the present invention, as well as pharmaceutically acceptable salts thereof.

The steroidal anti inflammatory drug is preferably a corticosteroid selected from the group consisting of: cortisone, hydrocortisone, deltacortisone, prednisolone, prednisone, deltahydrocortisone, prednisolone, methylprednisolone, medrocortisone, fluorohydrocortisone, fluorocortisone, fluoromethylprednisolone, dexamethazone, fluoromethyl-deltahydrocortisone, betamethasone, paramethazone, their pharmaceutically acceptable salts, and mixtures thereof.

Examples of non steroidal anti inflammatory drug encompass compounds selected from the group consisting of: aspirin, arylalkanoic acids, bromfenac, indometacin, oxameticin, 2-arylpropionic acids, fenbufen, pirprofen, ketoprofen, ibuprofen, oxaprozin, and ketorolac, femamic acids, pyrazolidine derivatives, clofezonem, kebuzone, phenazone, ocicams, droxicam, meloxicam, COX-2 inhibitors, celecoxib, rofecoxib, their pharmaceutically acceptable salts, and mixtures thereof.

An example of proteolytic enzyme is serrapeptase.

The invention encompass all pharmaceutically acceptable salts of the compounds disclosed herein, including in their generic appellation, and all mixtures thereof (disclosed active principles and salts). In particular. The terms "magnesium" and "potassium" encompass respectively any form of magnesium and potassium, and especially a pharmaceutically acceptable salt of magnesium and potassium, for example, magnesium chloride and potassium chloride.

"Consisting essentially or as used herein means that the composition can have the recited active principle(s) and optionally pharmaceutically acceptable vehicles, as well as additional ingredients that do not interfere with the activity of" the pharmaceutically active principle. Accordingly, minor ingredients can be added without having a major effect on active principles used in a composition, a medicament, a kit or a method as disclosed herein.

By "several", it is meant herein at least two (i.e., two or more than two) and, for example, three, four, five, six, seven, eight, nine, ten or more than ten.

According to a particular embodiment, the composition for therapeutic use consists essentially of or consists of Salbutamol or a pharmaceutically acceptable salt thereof.

According to a particular embodiment, the composition for therapeutic use comprises or consists essentially of or consists of: Salbutamol, N Acetyl DL Leucine, magnesium, potassium and nitric monoxide donor(s) as disclosed herein, or pharmaceutically acceptable salts thereof.

According to a particular embodiment, the composition for therapeutic use comprises or consists essentially of or consists of: Salbutamol, angiotensin converting enzyme inhibitor(s) as disclosed herein, aldosterone receptor antagonist(s) as disclosed herein, N Acetyl DL Leucine, magnesium, and proteolytic enzyme as disclosed herein, or pharmaceutically acceptable salts thereof.

According to a particular embodiment, the composition for therapeutic use comprises or consists essentially of or consists of: Salbutamol, angiotensin converting enzyme inhibitor(s) as disclosed herein, aldosterone receptor antagonist(s) as disclosed herein, N Acetyl DL Leucine, or pharmaceutically acceptable salts thereof.

According to a particular embodiment, the composition for therapeutic use comprises or consists essentially of or consists of: Salbutamol, angiotensin converting enzyme inhibitor(s) as disclosed herein and aldosterone receptor antagonist(s) as disclosed herein, or pharmaceutically acceptable salts thereof.

According to a particular embodiment, the composition for therapeutic use comprises or consists essentially of or consists of: Salbutamol, ramiprilate and eplerenone, It is observed that ramiprilate and eplerenone are active principles acting as inhibitors of the renin-angiotensin-aldosterone system (RAAS). The invention encompass the use of such compounds, possibly in association with further active ingredients as disclosed in any one of the embodiments of the present disclosure.

According to a particular embodiment, the composition for therapeutic use comprises or consists essentially of or consists of: Salbutamol, ramiprilate, eplerenone and N Acetyl DL Leucine.

According to particular embodiments, the compositions for therapeutic use of the present invention Therefore associate, according to the provisions provided herein, e.g., combinations or associations, active principles having functional effect, especially inhibitory effect, on the renin-angiotensin-aldosterone system (RAAS).

A composition for use according to the present disclosure can further comprise pharmaceutically acceptable additive(s), diluent(s) or vehicle(s) or carrier(s).

The term "pharmaceutically or ophthalmologically acceptable additive(s), diluent(s) or vehicle(s) or carrier(s)" as used herein means any ingredient or vehicle that has substantially no long term or permanent detrimental effect on the organ to which it is administered, especially the eye, in particular, any vehicle that can be placed on said organ, especially in the eye and that does not cause irritation, especially eye irritation. According to a particular embodiment where the encompassed pharmaceutically vehicles of the invention are opthamologically vehicles, they include water (distilled or deionized water), saline solutions, phosphate buffered saline solutions, physiological serum, and other aqueous media.

Otherwise, the pharmaceutically acceptable vehicle can be any acceptable carrier, adjuvant or vehicle that does not interfere with the pharmaceutical activity of an ophthalmic composition and is not toxic to the host to which the composition is administered. It includes solvents, dispersion media, coatings, absorption delaying agents and the like. These pharmaceutically acceptable vehicles are described in Remington's Pharmaceutical Sciences $21^{st}$ edition 2005. An acceptable vehicle can be, for example, saline, buffered saline and the like. It can be added to the pharmaceutical composition after its formulation.

According to a particular embodiment, the therapeutic composition of the invention as disclosed in any one of the embodiments described herein, in all disclosed combinations and associations, is for use in a method of preventing and/or treating one or several ophthalmic disease(s) involving a deterioration of the eye and/or of the visual function.

Accordingly, in a particular embodiment, the compositions of the invention are ophthalmic compositions, especially but not only when they are applied directly to the eye.

The term "vision" or "visual function" as used herein encompasses visual acuity (more especially near and/or far visual acuity) as well as contrast vision, color vision and field of vision (or visual field).

The term "loss of vision" or "degradation of visual function" as used herein includes partial or total loss of vision, and especially a partial or total loss in visual acuity (near and/or far visual acuity) and/or contrast vision and/or color vision and/or field of vision. It can result from a "natural" visual decline (i.e., it appears in the absence of any apparent eye disease or disorder), for example, in an aging animal, and/or from one or several ophthalmic condition(s) (in particular, an eye disorder and/or an eye disease) as disclosed herein.

By visual function it is accordingly and in particular meant visual acuity or visual field. Visual acuity is the clarity or sharpness of vision, which depends on the sharpness of the retinal focus within the eye. A classic Snellen chart is used to test visual acuity. Normal visual acuity is referred to as 20/20 vision, the metric value being 6/6 vision. The first number refers to the distance at which the patient's vision is tested, which is general 20 feet or 6 meters. The second number indicates the distance in which a normal eye can see the symbol or letter on the chart.

Visual field is determined through visual field testing the full horizontal and vertical range of what a patient is able to see peripherally. This type of testing is usually performed with an automated perimetry test in which the patient stares at a source of light straight ahead and random lights of different densities are flashed in their peripheral field of vision. The patient presses a button or other means to indicate that they can see the light.

"To ameliorate the visual function" means that the vision of an individual is improved from its initial state. To "maintain" it means that no worsening of the visual function is observed.

Ophthalmic disease(s) that can be prevented and/or treated according to the present disclosure may accordingly involve a deterioration of the eye (physiologic cause) and/or of the visual function.

The terms "treating" and "treatment" mean that an ophthalmic condition (in particular, an eye disorder and/or an eye disease) is improved (at least partially) and, in particular, that the visual acuity and/or the contrast vision and/or the color vision and/or the field of vision of the treated animal is improved, or that the process of degradation of visual function is stopped.

According to a particular embodiment, the invention is aimed or further aimed at maintaining or improving the visual function, in particular the visual acuity and/or visual field, of a subject in need of such treatment.

As used herein, the term "ophthalmic conditions or disease(s)" (or eye conditions) encompasses ophthalmic disorders and ophthalmic diseases involving chorio-retinal and/or optic nerve, resulting in a progressive loss of vision.

Are especially encompassed chronic ophthalmic diseases.

The term "ophthalmic disorder" (or eye disorder) as used herein encompasses a change in vision, in the appearance of the eye or having abnormal sensations in the eye. It includes optic nerve disorders and chorio-retinal disorders, as well as trauma such as injuries to the eye, and especially disorders resulting in a progressive visual degradation or loss of vision.

According to the present disclosure, said ophthalmic disease(s) is(are) selected from the group comprising: hereditary dystrophies of the retina, glaucoma, glaucoma neuropathy, age related macular degeneration, ametropia, dry eye, hereditary dystrophies of ocular inflammation, ocular inflammation, uveitis, orbital inflammation, cataract, allergic; conjunctivitis, diabetic retinopathy, macular oedema, corneal oedema, keratoconus, proliferative vitreo retinopathy (fibrosis), peri-retinal fibrosis, central serious chorio retinopathy, vitreo retinal pathology, vitreo macular traction and vitreous hemorrhage.

According to particular embodiments, hereditary dystrophies of the retina are selected amongst: pigmentosa retinitis and Stargardt's disease.

According to particular embodiments, ametropia is selected amongst: presbyopia, myopia and hypermetropia:

According to a particular embodiment, the invention is aimed at preventing and/or treating vitreo macular traction in order to trigger a vitreolysis in vitreo retinal pathology.

The term "subject" or "animal" as used herein includes mammalians, in particular, humans and non human mammalians.

According to particular aspects, the composition for use described herein can be administered orally, parentally, intravenously, intravascularly, intramuscularly, transdermally, or topically (including through intra-ocular injection).

A composition of the invention can generally be in the form of a solid or a solution.

According to a particular embodiment, the composition is administered topically to the eye, especially through eye drops or intraocular infection or intravitreal injection.

By "topical administration" it is meant herein an administration which has a local effect. This term includes especially a sub-tenonian administration, or an administration to the eye (especially an intra- or extra-ocular administration).

By "topical form", it is accordingly meant herein a form appropriate for topical administration, and especially a solution (in particular, an ophthalmic solution), a lotion, drops (in particular, eye drops), a cream or an ointment.

The administration to the eye can be performed, for example, by applying active principle(s) as disclosed herein (which can be, for example, in the form of an ophthalmic solution, an ointment or eye drops) to the outside surface of the eye, i.e., by contacting the eye and especially the cornea with said active principle(s).

Alternatively or cumulatively, the administration to the eye can be performed by injecting active principle(s) into the eye and especially into the vitreous (La, via intravitreal injection), for example, in the form of an ophthalmic solution.

Active principles can be administered to the eye (for example, by application to the outside surface of the eye and/or by intraocular injection) using a delivery device which provides a controlled release of active principle(s) on the surface of the eye or into the eye. Said device can be, for example, placed in the lower cul de sac or conjunctival cul-de-sac, below the cornea, or injected into the eye, especially into the vitreous.

According to a particular embodiment, the composition is in the form of a solution, a lotion, drops, a cream or an ointment. According to a more particular embodiment, the composition is in the form of an ophthalmic solution or eye drops. In a particular implementation of the invention, the composition is administered as eye drops into the eye(s).

According to a particular aspect, the compositions described herein encompass those disclosed in the Examples section, but also encompass the following embodiments, according to all possible combinations thereof, wherein the active principle(s) are administered as follows:

Salbutamol is administered topically in a concentration ranging from 0.05 to 2% (w/v), or ranging from 0.05 to 1% (w/v), or ranging from 0.1 to 2% (w/v), or ranging from 0.1 to 1% (w/v), or ranging from 0.5 to 2% (w/v), or ranging from 0.5 to 1% (w/v), in particular Salbutamol is administered at a concentration of 0.1, or 0.5, or 1 or 2% (w/v), and/or Ramiprilate is administered topically in a concentration ranging from 0.5 to 5% (w/v), or ranging from 0.5 to 3% (w/v), or ranging from 0.5 to 2% (w/v), for example at a concentration of 0.5%, or 1% or 2% (w/v), and/or eplerenone is administered topically in a concentration ranging from 0.5 to 5% (w/v), or ranging from 0.5 to 3% (w/v), or ranging from 1 to 2% (w/v), for example at a concentration of 0.5%, or 1% or 2% (w/v), and/or N Acetyl DL Leucine is administered topically in a concentration ranging from 0.5 to 5% (w/v), or ranging from 0.5 to 3% (w/v), or ranging from 1 to 2% (w/v), for example at a concentration of 0.5%, or 1% or 2% (w/v).

The skilled person can readily practice the invention within these ranges, observing the produced effect.

According to particular embodiments, Salbutamol is administered topically in a concentration of 0.1% (w/v), and/or Ramiprilate is administered topically in a concentration of 2% (w/v), and/or eplerenone is administered topically in a concentration of 1% (w/v), and/or N Acetyl DL Leucine is administered topically in a concentration of 1% (w/v).

It will be appreciated that according to a particular embodiment, the active principle(s) is(are) administered once or twice or three times, and up to four times a day.

According to a particular embodiment, the active principle(s) is (are) administered during 1, 2 or 3 months, or more.

The compositions or medicaments that contain the active principles as defined therein may be administered to a mammalian eye as often as necessary to obtain an improvement of the disorder or disease (and especially of the ophthalmic condition).

Those skilled in the art will recognize that the frequency of administration and duration of treatment depends on the precise nature of the active principles and its concentration in the composition, and various factors such as the type and severity of the disorder or disease, the age and weight of the animal, the animal's general physical condition and the cause of the disorder or disease. Within these guidelines, it is contemplated that the ophthalmic composition (preferably ophthalmic solutions or eye drops) of the present invention will be administered topically to the mammalian eye and, in particular, dropped into the eye and/or injected into the mammalian eye approximately once, twice or three times daily.

The duration of treatment administered in accordance with the present invention may range, for example, from a few weeks (at least one week) to a few months (at least one month), in particular, from 1 week to 6 months, and all intermediary values. The duration can range from at least 2 weeks to less than 4 months, especially 3 months, and can be reiterated with the same prescription or another (within the guidelines provided herein). A prolonged treatment may be required. In particular, the treatment may last for one or several years or even for life, for example, in case of recurrence of the disorder(s) or disease(s) and especially of an ophthalmic condition.

Of course, one of several additional active principle(s), and especially one of several additional compounds for treating eye disorders and/or diseases may be used in the methods of the invention or may be present in a composition, a medicament or a kit according to the invention, provided that they do not interact with the other active principles, to provide adverse side effects.

According to another aspect, the active principle(s) is (are) found within a single composition or in separate compositions.

It will be apparent from the present description that all disclosed active principles can be are administered separately (i.e., in separate compositions) or not separately (for example, in the same composition).

More precisely, according to particular embodiment, the active principles are administered simultaneously or separately, or sequentially, to a subject in need thereof. The skilled person can readily determined whether the administered active principles may be found in a same composition according to the defined protocol.

By "sequentially", it may be meant that the active principles are administered in a particular order at a particular application time (according to the schedule disclosed above), the order being commonly defined by the skilled person, or that that two or several rounds of treatment protocols are successively carried out over an extended period of time corresponding to two or several period of time as disclosed herein.

The compositions involved in the several rounds of treatment may be different from one round with respect to another round, or be the same (reiteration). Also, formulations type or dosages may be different, or be the same, in said different rounds.

According to a particular embodiment, wherein several active principles found in one or several compositions are administered sequentially over time to a subject in need thereof, the following scheme may be followed:

Salbutamol is administered topically once or twice or three times, and up to four times a day, during 1, 2 or 3 months, or more, and then Salbutamol, ramiprilate, eplerenone and N Acetyl DL Leucine are simultaneously, sequentially or separately administered topically once or twice or three times, and up to four times a day, during 1, 2 or 3 months, or more, or Salbutamol, ramiprilate and eplerenone are simultaneously, sequentially or separately administered topically once or twice or three times, and up to four times a day, during 1, 2 or 3 months, or more.

Examples of sequential administration are provided in the Examples section below.

The invention also relates to a method for preventing and/or treating one or several ophthalmic disease(s) or disorder(s) involving a deterioration of the eye and/or of the visual function, comprising administering to a subject in need thereof a composition comprising at least Salbutamol or a pharmaceutically acceptable salt thereof.

According to a particular embodiment, said method further comprises administering one or several active principle(s) or composition(s) as defined in any one of the embodiments disclosed herein, wherein said several active principles are administered simultaneously, sequentially or separately, within a single or several separate composition(s), according to the definitions provided herein.

According to a particular embodiment, the method of the invention comprises administering to a subject in need thereof according to the definitions provided herein, a compositions that consists essentially of or consists of Salbutamol or a pharmaceutically acceptable salt thereof, optionally with pharmaceutically acceptable additive(s), diluent(s) or vehicle(s) or carrier(s). The administered active principle(s) are provided in an effective amount and/or pharmaceutically acceptable amounts (especially physiologically or ophtalmologically acceptable amounts) for therapeutic effect, as in particular disclosed herein.

The administered composition(s) and/or administered active principle(s) is(are) as disclosed in any one of the embodiments recited herein.

The subject in need thereof has one or several ophthalmic disease(s) as defined herein. Administration routes, galenic formulations, dosages, concentrations, posologies, treatment schedules or protocols are as disclosed hereabove.

Accordingly, several active principles can be administered simultaneously, sequentially or separately to a subject in need thereof.

According to a particular embodiment, the method of the invention is or is further for maintaining or improving the visual function, in particular the visual acuity and/or visual field, of a subject in need of such treatment.

The invention also relates to a composition, characterized in that it comprises or consists essentially of, or consists of
- Salbutamolv or a pharmaceutically acceptable salt thereof, and
- One or several active principle(s) selected from the group consisting of: beta 1 adrenergic blockers, alpha 2 adrenergic agonists, anhydrase carbonic inhibitors, angiotensin converting enzyme inhibitors (Ramiprilat), aldosterone receptor antagonist (eplerenone). N Acetyl DL Leucine, glucose, magnesium, potassium, nitric monoxide donors (vitamin C, vitamin B9), steroidal anti inflammatory drugs, non steroidal anti inflammatory drugs, proteolytic enzyme (serrapeptase), one of their pharmaceutically acceptable salts thereof, and mixtures thereof, and
- Optionally, pharmaceutically acceptable additive(s), diluent(s) or vehicle(s) or carrier(s).

According to particular embodiments, all compositions disclosed herein according to all possible combinations of active ingredients, formulations suited to specific administration routes, dosages, concentrations, and posologies are part of the present invention and disclosure.

The invention also relates to a kit of parts of a first active principle that is Salbutamol or a pharmaceutically acceptable salt thereof, with one or more active principle(s) as defined herein, wherein said active principles are capable of providing a joint effect when applied side by side, with some are all of the ingredients found in admixture or separately.

According to a particular embodiment, the invention provides a kit of parts of a first active principle that is Salbutamol or a pharmaceutically acceptable salt thereof, with one or more active principle(s) having functional effect, especially inhibitory effect, on the renin-angiotensin-aldosterone system (RAAS), as disclosed herein. Reference to the mechanisms of action described herein is made.

The invention also relates to a kit comprising or consisting essentially of or consisting of:
- At least two active principles as defined according to all embodiments described herein, and
- Optionally, instructions for using said kit,
wherein the active principles of the kit are associated in a same composition or wherein at least two or more of these active principles are in separate compositions.

The composition(s) or kit of parts or kit(s) of the invention can be used in a method of the invention as disclosed herein. They can be used as a protective ophthalmic medicament, especially for a treatment as disclosed herein.

The invention also relates to the use of a composition, kit-of-parts or a kit disclosed herein, in the manufacture of a medicament intended for use as defined in any embodiment herein.

The invention also relates to the use of Salbutamol or a pharmaceutically acceptable salt thereof, in the manufacture of a protective ophthalmic medicament as defined in any one of the embodiments disclosed herein.

The invention also relates to a composition, in particular, to a pharmaceutical composition (or drug or medicament) characterized in that it comprises, consists essentially of or consists of beta 2 adrenergic agonist for example Salbutamol, one or several additional active principle chosen among: non steroidal anti inflammatory agent, an N Acetyl DL Leucine, an angiotensin converting enzyme inhibitor (also called ACEI herein), aldosterone receptor antagonist (eplerenone), folic acid and magnesium.

The association: β2 Adrenergic agonist, N Acetyl DL Leucine, potassium, nitric monoxide donor (vitamin C, vitamin B9), magnesium is also remarkable.

In an embodiment of the invention, the invention relates to a oculo-protective medicament which is suitable for improving far and near vision, reversing the course of presbyopia, preventing, slowing down or interrupting the process of vision loss or even reversing its course in an animal (especially a human or non human mammal and in particular, in an aging animal and in an animal with one or several eye ophthalmic condition (s).

In an embodiment of the invention, the composition or medicament for and/or used for maintaining or improving vision in an animal, and in particular, in an aging animal and/or in an animal with an eye disease or disorder.

EXAMPLES—CLINICAL OBSERVATIONS

The invention will be illustrated further by the description of clinical examples, which of course are not limiting in nature. The medicament was administrated orally, topically in the form of eye drops or by intraocular injection especially intravitreal injection, unless indicated differently.

According to particular embodiments where topical administration using eye drops is carried out, the dosages, posologies, administration regimen of the administered active principles are as described in the particular embodiments disclosed in the detailed description, i.e., Salbutamol is administered topically in a concentration of 0.1% (w/v), and/or Ramiprilate is administered topically in a concentration of 2% (w/v), and/or eplerenone is administered topically in a concentration of 1% (w/v), and/or N Acetyl DL Leucine is administered topically in a concentration of 1% (w/v), the active principle(s) being administered once or twice or three times, and up to four times a day, during 1, 2 or 3 months, or more, unless specified differently.

1) Ametropia:

This invention relates to the manufacture of an eye protective medicament, namely Salbutamol via general route or topical route (eye drops) for improving vision.

More particularly, but not exclusively, it relates to eye drops comprising Salbutamol, which are intended for improving (i.e., in the present case decreasing the effects of presbyopia, myopia, hypermetropia and astigmatism) and for stabilizing them or even reversing their evolutive course thereof.

In all of these cases of ametropia the result improves if we associate glucose and/or magnesium and/or potassium and/or N Acetyl DL Leucine and/or converting enzyme inhibitor and/or α2 adrenergic agonist and/or nitric monoxide donor (vitamin C, vitamin B9).

Myopia:

12 patients were evaluated and received salbutamol in the form of eye drops.

Results: in the addition to the improvement of their visual acuity, the refractive value was reduced. One can deduce that Salbutamol not only improve vision but also treat myopia.

Presbyopia:

Presbyopia is a condition associated with aging of the eye that results in progressively worsening ability to focus clearly on close objects. Symptoms include a hard time reading small print, having to hold reading material farther away, headaches, and eyestrain. Different people will have different degrees of problems. Other types of refractive errors may exist at the same time as presbyopia.

Presbyopia is a natural part of the aging process. It is due to hardening of the lens of the eye causing the eye to focus light behind rather than on the retina when looking at close objects. It is a type of refractive error along with nearsightedness, farsightedness, and astigmatism. Diagnosis is by an eye exam.

Treatment is typically with eye glasses. The eyeglasses used have higher focusing power in the lower portion of the lens. Off the shelf reading glasses may be sufficient for some.

People over 35 are at risk for developing presbyopia and all people become affected to some degree. The condition was mentioned as early as the writings of Aristotle in the 4th century BC. Glass lenses first came into use for the problem in the late 13th century.

The first symptoms most people notice are difficulty reading fine print, particularly in low light conditions, eyestrain when reading for long periods, blurring of near objects or momentarily blurred vision when transitioning between viewing distances. Many extreme presbyopes complain that their arms have become "too short" to hold reading material at a comfortable distance.

Presbyopia, like other focal imperfections, becomes less noticeable in bright sunlight when the pupil becomes smaller. As with any lens, increasing the focal ratio of the lens increases depth of field by reducing the level of blur of out-of-focus objects (compare the effect of aperture on depth of field in photography). The onset of correction for presbyopia varies among those with certain professions and those with miotic pupils. In particular, farmers and homemakers seek correction later, whereas service workers and construction workers seek eyesight correction earlier. Scuba divers with interest in underwater photography may notice presbyopic changes while diving before they recognize the symptoms in their normal routines due to the near focus in low light conditions 08 patients received Salbutamol in the form of eye drops and experimented an improvement of their near vision and a decrease in presbyopia. Some of them did not need any longer to wear a correction of the near vision. Salbutamol has proven to be an effective treatment of presbyopia.

09 patient are treated by the association: Salbutamol, N Acetyl DL Leucine, magnesium, potassium, nitric monoxide donor (vitamin C, vitamin B9) and demonstrate a better results in term of near vision.

Astigmatism:

The astigmatism subjects noticed an improvement of their refraction and visual acuity.

Keratoconus:

02 patients received Salbutamol, they noticed an improvement of visual acuity and a reduced irregular astigmatism.

2) Diabetic Retinopathy:

Diabetic retinopathy, also known as diabetic eye disease, is a medical condition in which damage occurs to the retina due to diabetes. It can eventually lead to blindness.

It affects up to 80 percent of people who have had diabetes for 20 years or more. At least 90% of new cases could be reduced if there were proper treatment and monitoring of the eyes. The longer a person has diabetes, the higher his or her chances of developing diabetic retinopathy. Each year in the United States, diabetic retinopathy accounts for 12% of all new cases of blindness. It is also the leading cause of blindness for people aged 20 to 64 years.

Diabetic retinopathy often has no early warning signs. Even macular edema, which can cause rapid vision loss, may not have any warning signs for some time. In general, however, a person with macular edema is likely to have blurred vision, making it hard to do things like read or drive. In some cases, the vision will get better or worse during the day.

In the first stage which is called non-proliferative diabetic retinopathy (NPDR) there are no symptoms, the signs are not visible to the eye and patients will have 20/20 vision. The only way to detect NPDR is by fundus photography, in which micro aneurysms (microscopic blood-filled bulges in the artery walls) can be seen. If there is reduced vision, fluorescein angiography can be done to see the back of the eye. Narrowing or blocked retinal blood vessels can be seen clearly and this is called retinal ischemia (lack of blood flow).

Macular edema in which blood vessels leak their contents into the macular region can occur at any stage of NPDR. The symptoms of macular edema are blurred vision and darkened or distorted images that are not the same in both eyes. Ten percent (10%) of diabetic patients will have vision loss related to macular edema. Optical Coherence Tomography can show the areas of retinal thickening (due to fluid accumulation) of macular edema.

In the second stage, abnormal new blood vessels (neovascularisation) form at the back of the eye as part of proliferative diabetic retinopathy (PDR); these can burst and bleed (vitreous hemorrhage) and blur the vision, because these new blood vessels are fragile. The first time this bleeding occurs, it may not be very severe. In most cases, it will leave just a few specks of blood, or spots floating in a person's visual field, though the spots often go away after few hours.

These spots are often followed within a few days or weeks by a much greater leakage of blood, which blurs the vision. In extreme cases, a person may only be able to tell light from dark in that eye. It may take the blood anywhere from a few days to months or even years to clear from the inside of the eye, and in some cases the blood will not clear. These types of large hemorrhages tend to happen more than once, often during sleep.

On funduscopic exam, a doctor will see cotton wool spots, flame hemorrhages (similar lesions are also caused by the alpha-toxin of *Clostridium novyi*), and dot-blot hemorrhages.

Diabetic macular oedema is a principle cause of visual loss in diabetic patients.

Currently, one examination technique is very useful in evaluating diabetic; that's optical coherence tomography (O.C.T).

OCT is very sensitive in evaluating diabetic macular oedema, central macular thickness correlates with visual acuity.

The response of macular oedema to the administration of one drug such as Salbutamol or a medicament associating Salbutamol, angiotensin converting enzyme inhibitor, antagonist of aldosterone receptor and N Acetyl DL Leucine can be documented accurately by O.C.T imaging.

Diabetic patients were treated with these medicaments given topically,

The following study was undertaken on several patients having non-proliferative diabetic; retinopathy or proliferative diabetic retinopathy.

20 patients were treated with either Salbutamol or salbutamol associated with one or more of these: ACEI (angiotensin converting enzyme inhibitor), aldosterone receptor antagonist, N Acetyl DL Leucine, magnesium and serrapeptase (eye drops; tablets; intra ocular injection especially intra vitreal injection). All improves their retinopathy and visual acuity.

Figure 2:
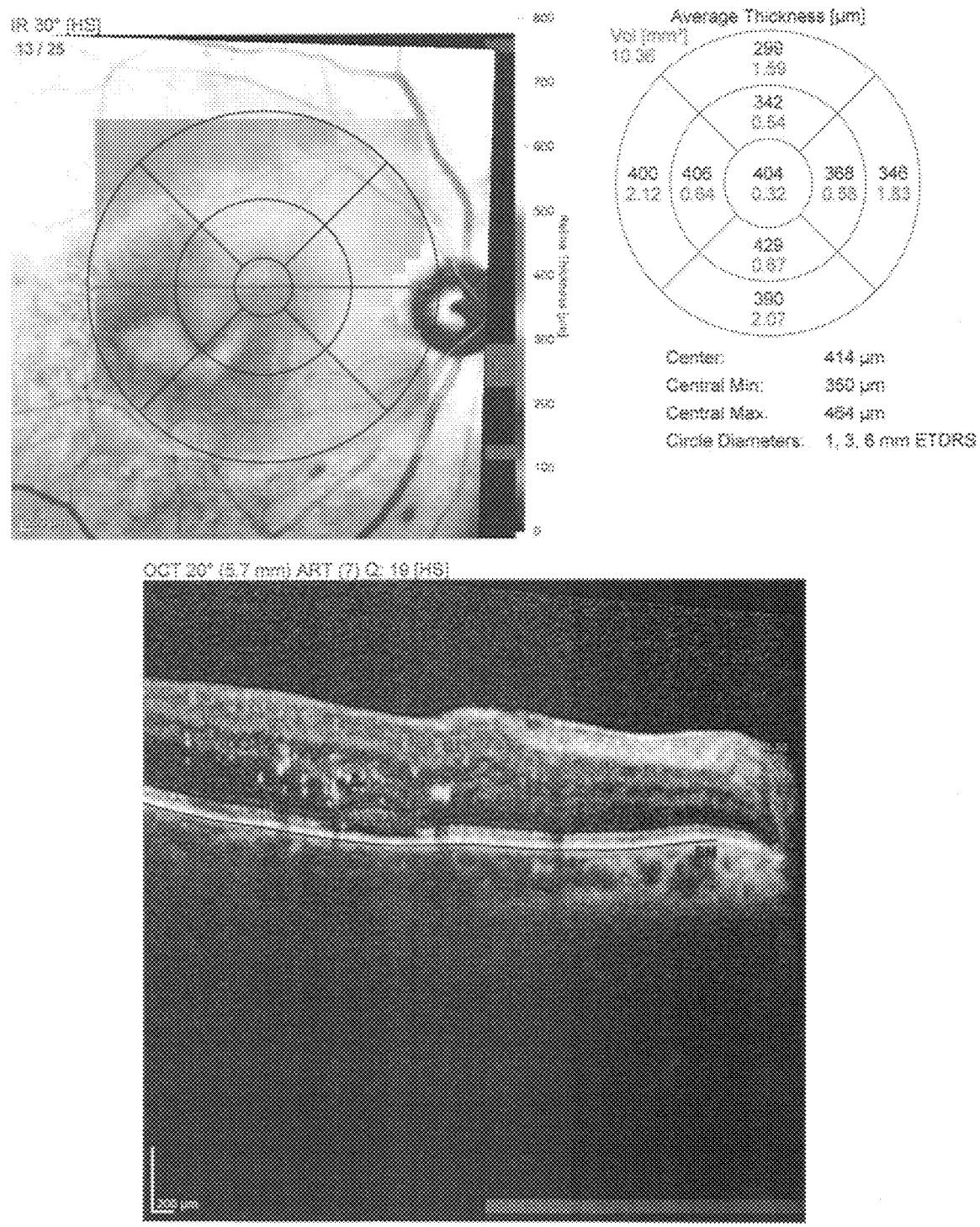
FIG. 2 is an optical coherence tomography scan (OCT) of patient B.Z., who has diabetic retinopathy, after treatment.
Figure 3:
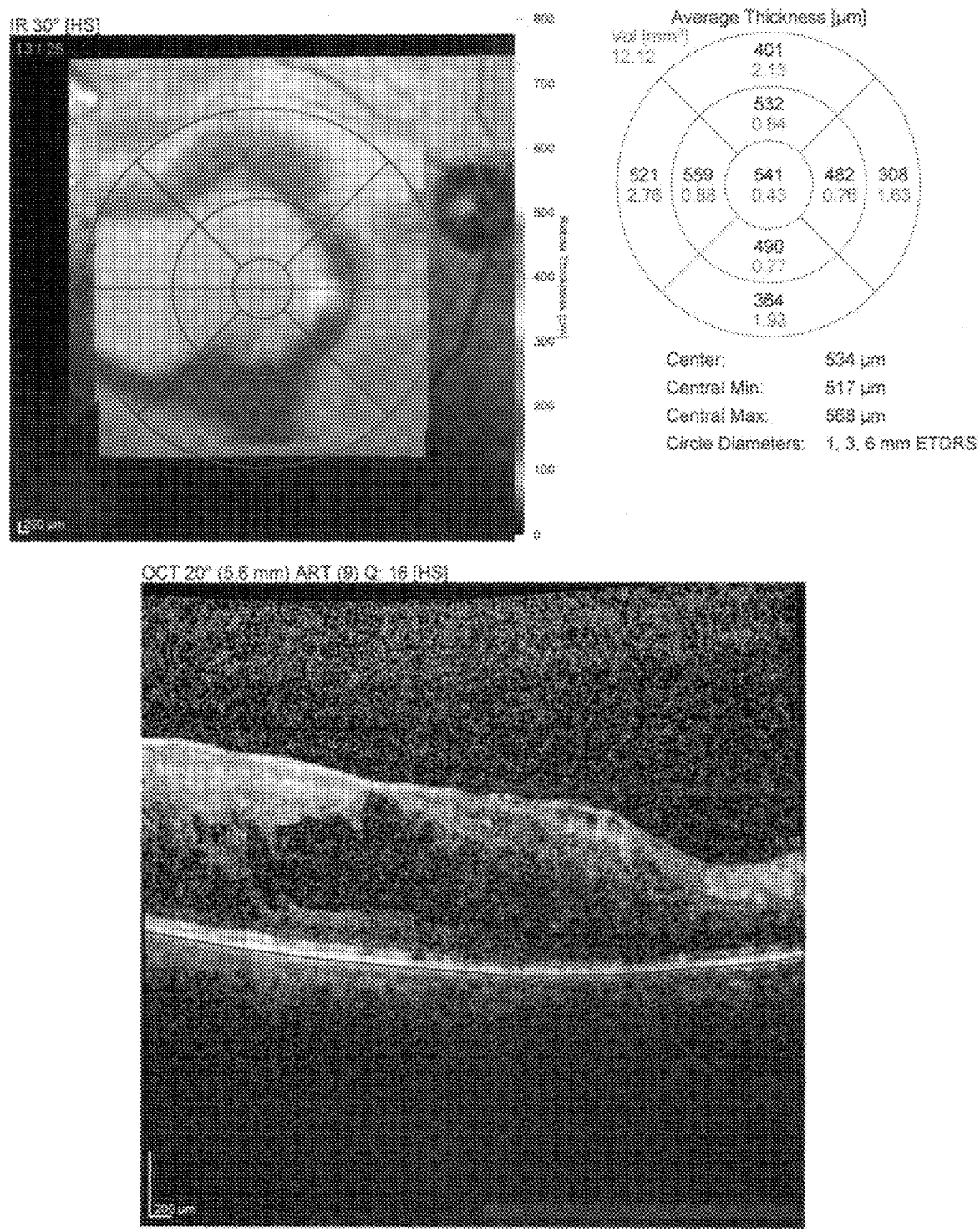
FIG. 3 is an optical coherence tomography scan (OCT) of patient B.M., who has non proliferative diabetic retinopathy, before treatment.
Figure 4:
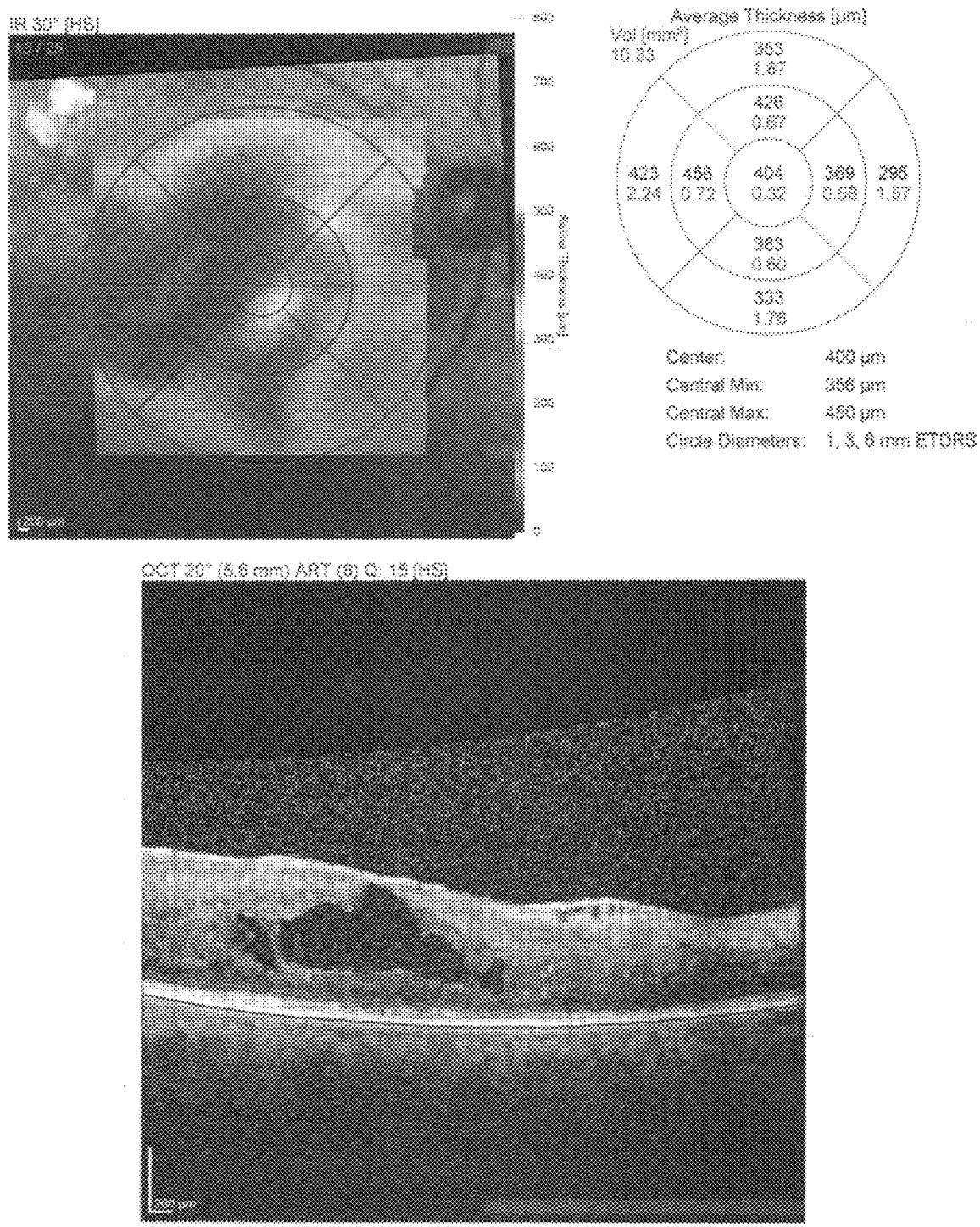
FIG. 4 is an optical coherence tomography scan (OCT) of patient B.M., who has non proliferative diabetic retinopathy, after treatment.

B.Z is a diabetic patient who presented a diabetic retinopathy (FIG. 01 OCT), She received topically (eye drops) 0.1% (w/v) Salbutamol. Two months after treatment a follow-up OCT scan (FIG. 02 OCT) showed that the total macular volume had decreased Patient B.M presented with a non proliferative diabetic retinopathy (FIG. 03 OCT). She received topically Salbutamol eye drops 0.1% (w/v) Ramiprilat eye drops 2% (w/v) Eplerenone eye drops 1% (w/v) N Acetyl DL Leucine eye drops 1% (w/v) three times a day. Three months later his visual acuity was improved. A follow-up OCT scan (FIG. 04 OCT) showed a high resolution of the intra retinal fluid.

3) Age Related Macular Degeneration

Age-related macular degeneration (AMD) is a problem with your retina. It happens when a part of the retina called the macula is damaged. With AMD you lose your central vision. You cannot see fine details, whether you are looking at something close or far. But your peripheral (side) vision will still be normal. For instance, imagine you are looking at a clock with hands. With AMD, you might see the clock's numbers but not the hands.

AMD is very common. It is a leading cause of vision loss in people 50 years or older.

Two types of AMD:
Dry AMD

This form is quite common. About 80% (8 out of 10) people who have AMD have the dry form. Dry AMD is when parts of the macula get thinner with age and tiny clumps of protein called drusen grow. You slowly lose central vision. There is no way to treat dry AMD yet.

Wet AMD

This form is less common but much more serious. Wet AMD is when new, abnormal blood vessels grow under the retina. These vessels may leak blood or other fluids, causing scarring of the macula. You lose vision faster with wet AMD than with dry AMD.

Many people don't realize they have AMD until their vision is very blurry. This is why it is important to have regular visits to an ophthalmologist. He or she can look for early signs of AMD before you have any vision problems.

The best proven therapies for ARMD treat the neovascular form of the disease and include photocoagulation and anti VEGF intra ocular injection (Avastin; lucentis).

The structural information provided by O.C.T is becoming a valuable diagnostic adjunct to fluorescein angiography. OCT is a valuable tool for probing the effect of these treatments.

Instead of an intraocular injection of an anti VEGF agent, Salbutamol given topically (eye drops 0.1% (w/v)) 3 times a day or Salbutamol, eplerenone 1% (w/v), Ramiprilat 2% (w/v) association eye drops demonstrate a macular thickening regression.

15 patients were treated with salbutamol or salbutamol associated with one or more of these: aldosterone receptor antagonist, ACEI (angiotensin converting enzyme inhibitor), N Acetyl DL Leucine, magnesium and serrapetase (Eye drops; tablets; intra ocular injection).

They noticed an improvement of the O.C.T and their visual acuity.

Figure 5:
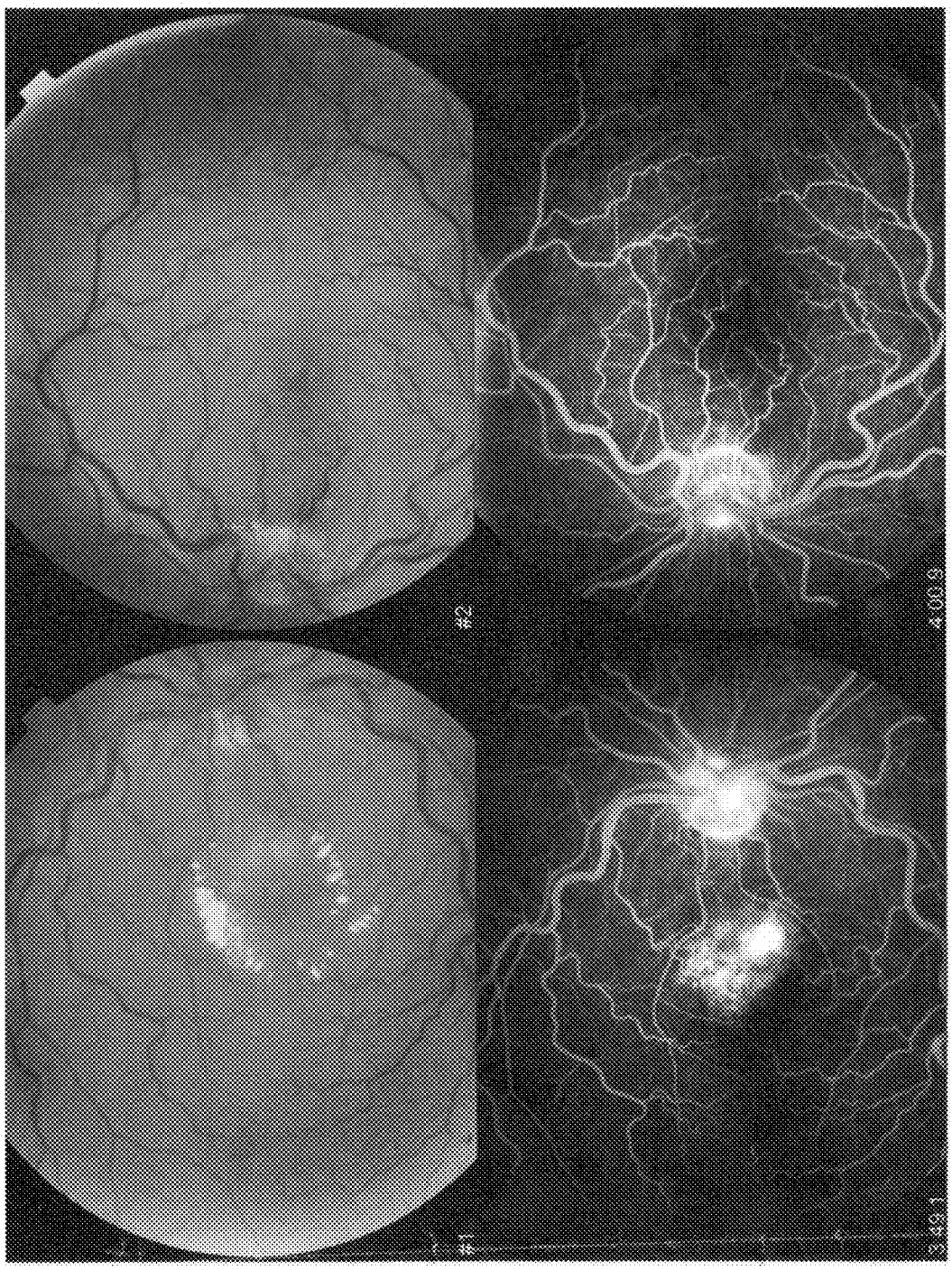
FIG. 5 is a fluoangiography of patient M.E., who has ARMD.
Figure 6:
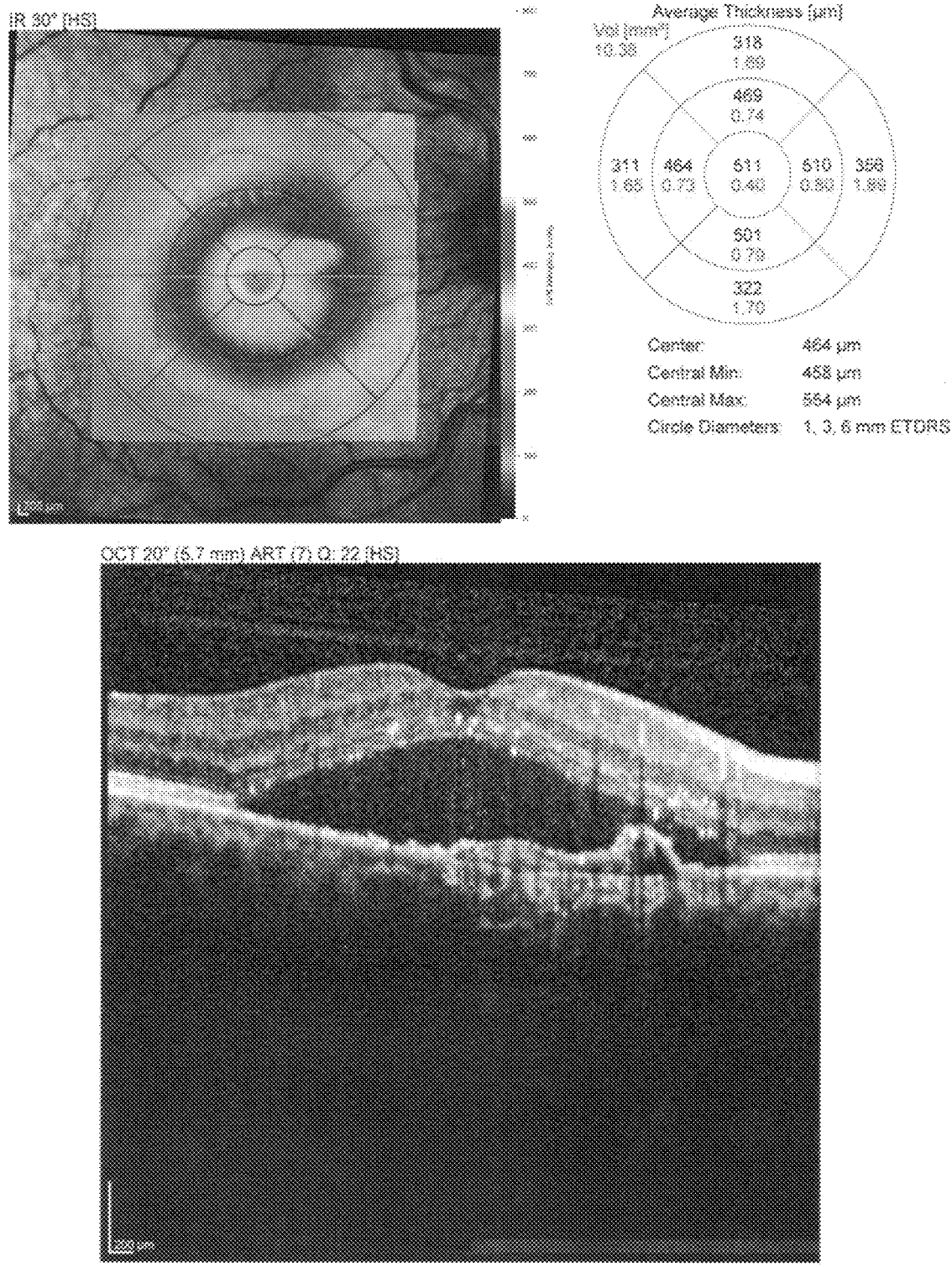
FIG. 6 is an optical coherence tomography scan (OCT) of patient M.E., who has ARMD, before first round of treatment.

Patient M.E presented with a history of decreased vision in the right eye. A fluoro-angiography image (FIG. 05) showed choroidal occult new vessel (CNV). Prior to receiving Salbutamol treatment an OCT scan was taken, which is shown in (FIG. 06). Three months later vision demonstrated an incomplete regression of macular thickening.

Figure 7:
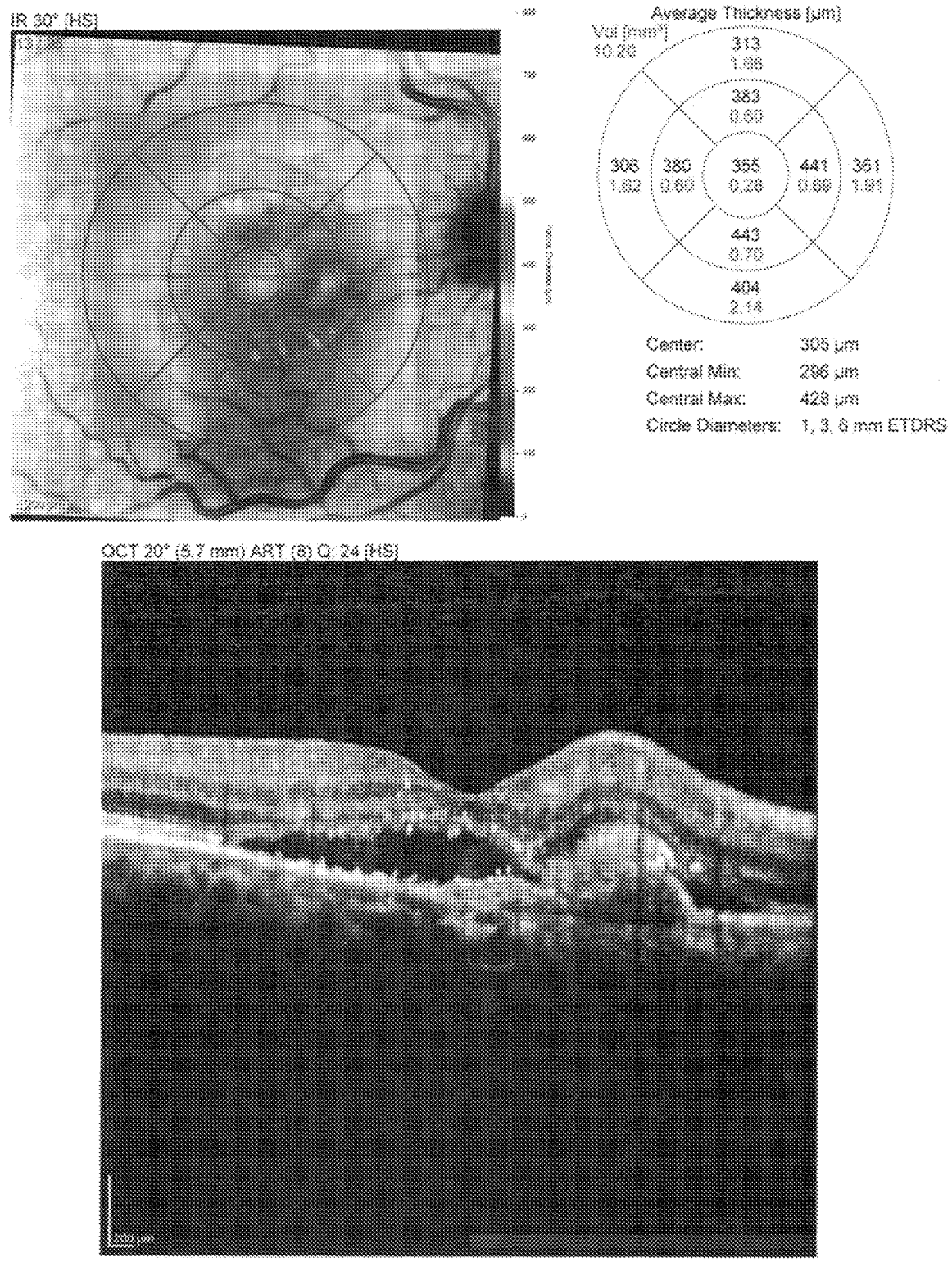
FIGS. 7 to 9 are optical coherence tomography scans (OCT) of patient M.E., who has ARMD, after first round of treatment.
Figure 8:
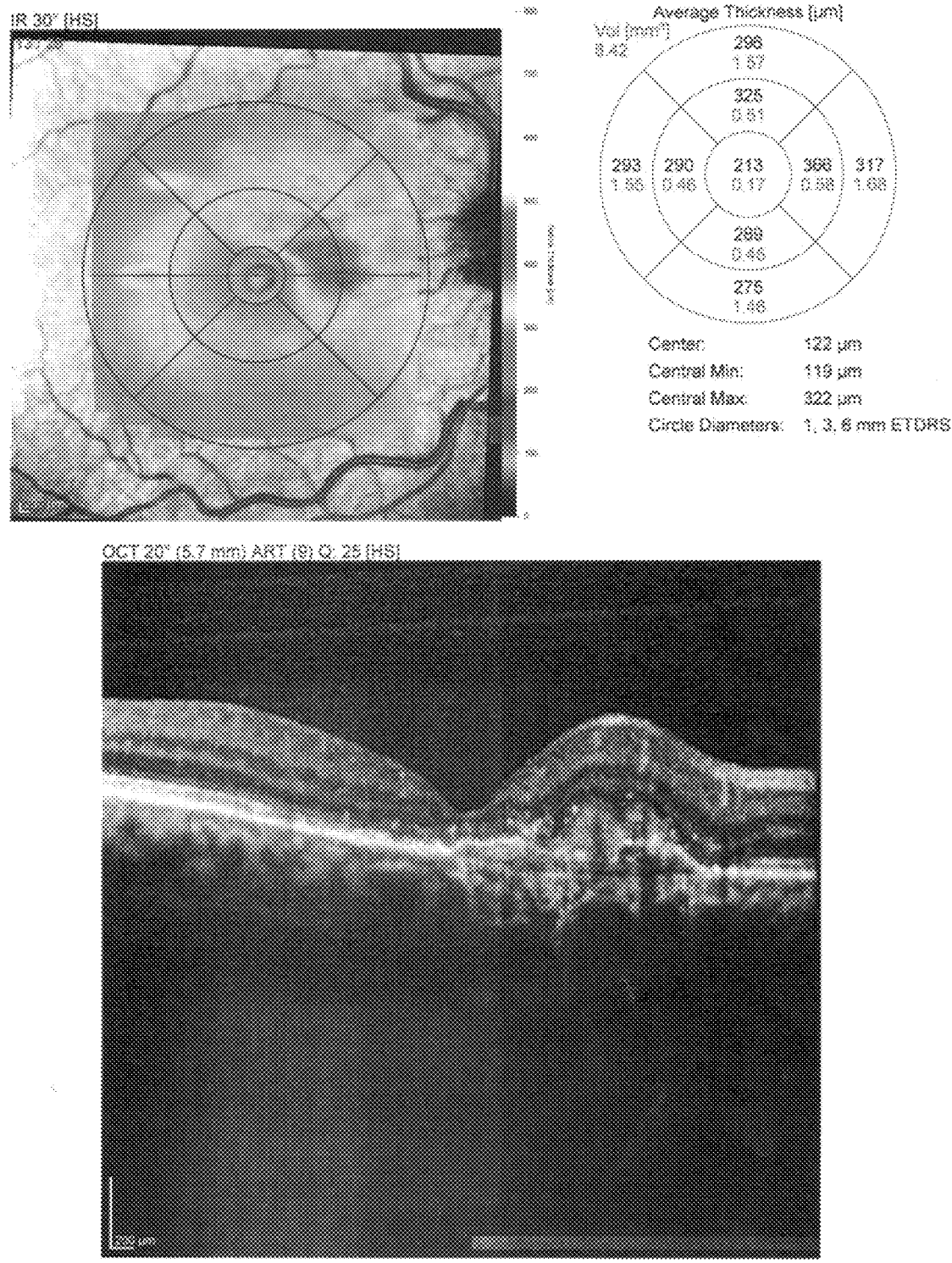
Figure 9:
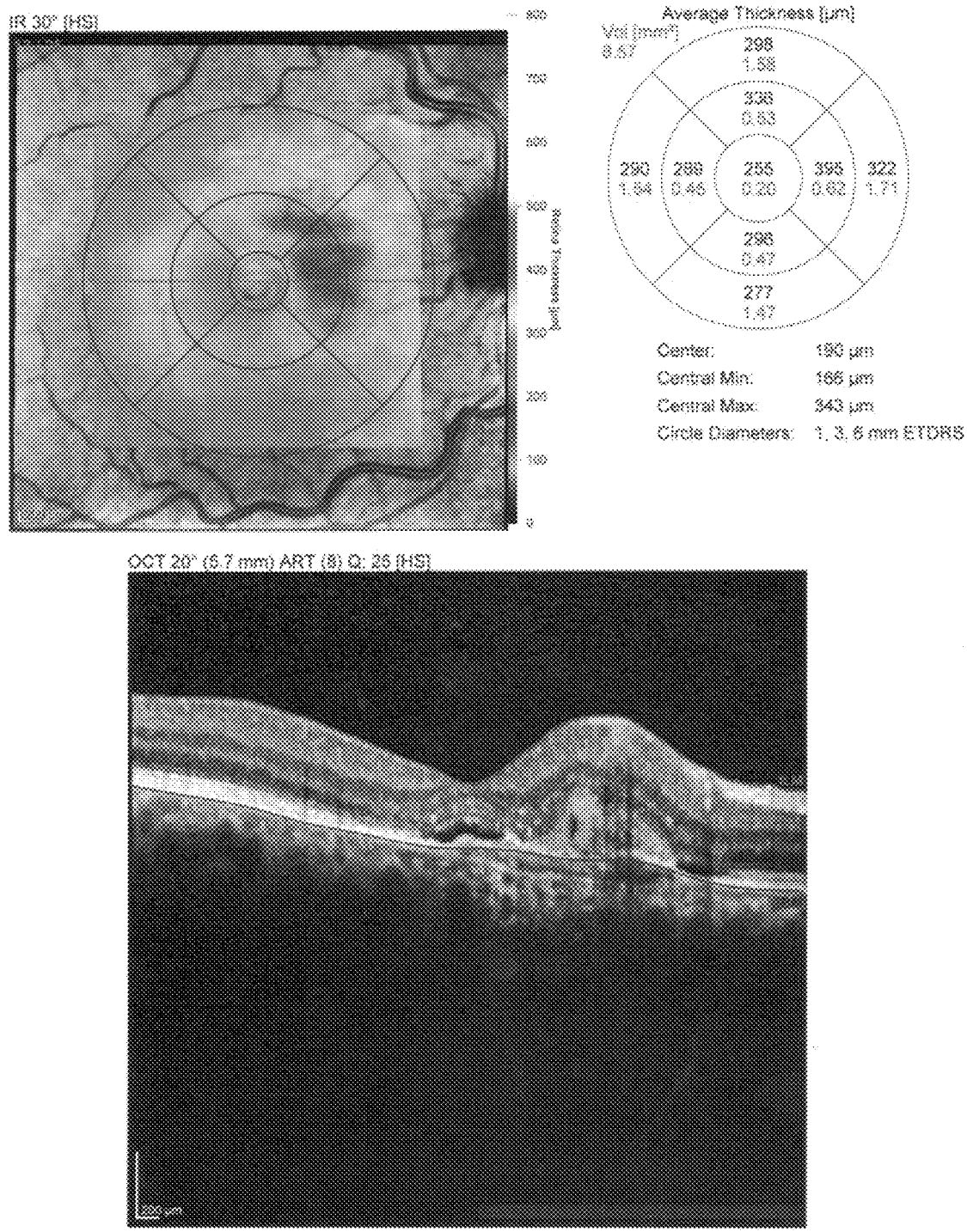
Figure 10:
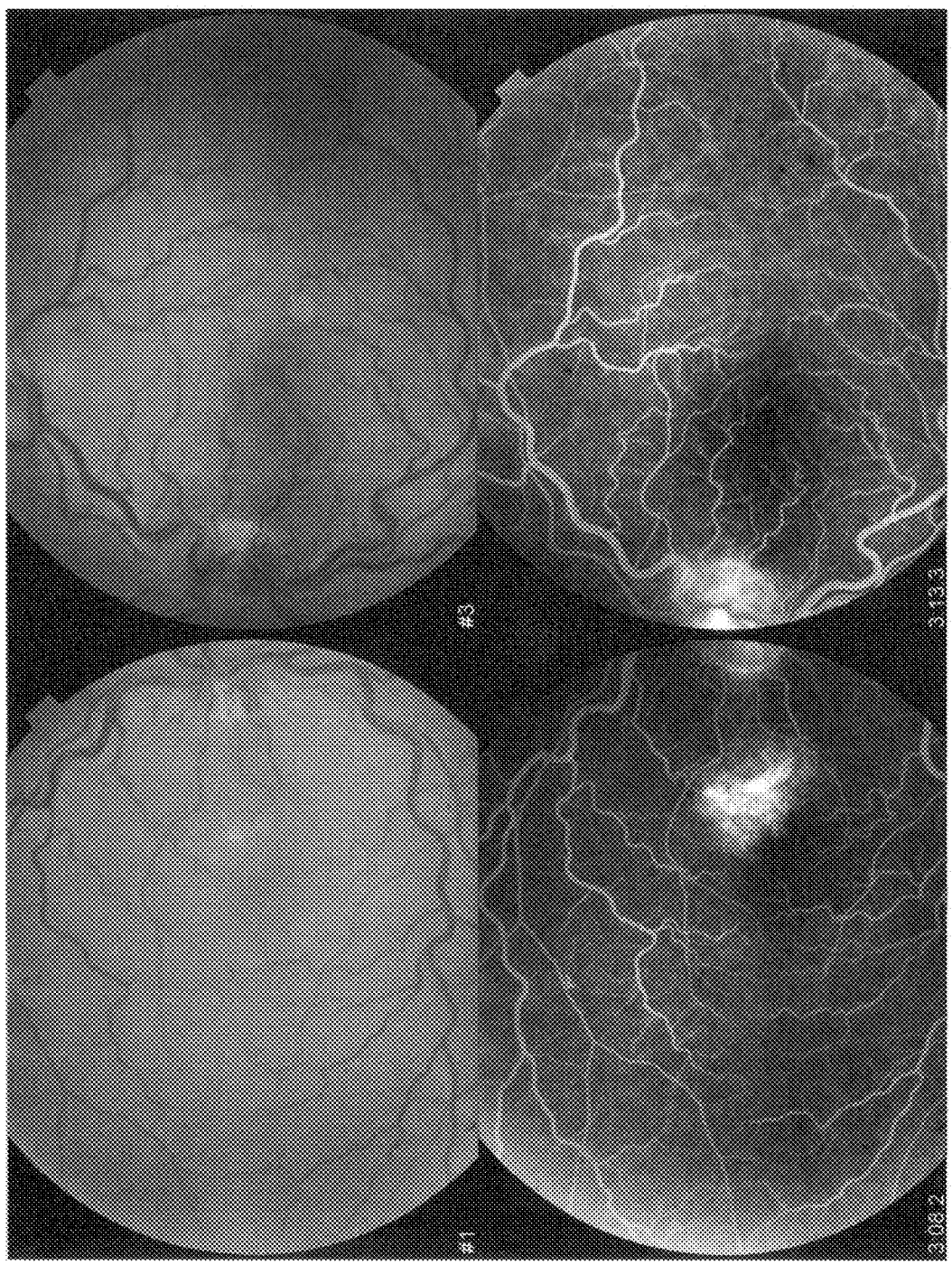
FIG. 10 is a fluoangiography of patient M.E., who has ARMD, after second round of treatment.
Figure 11:
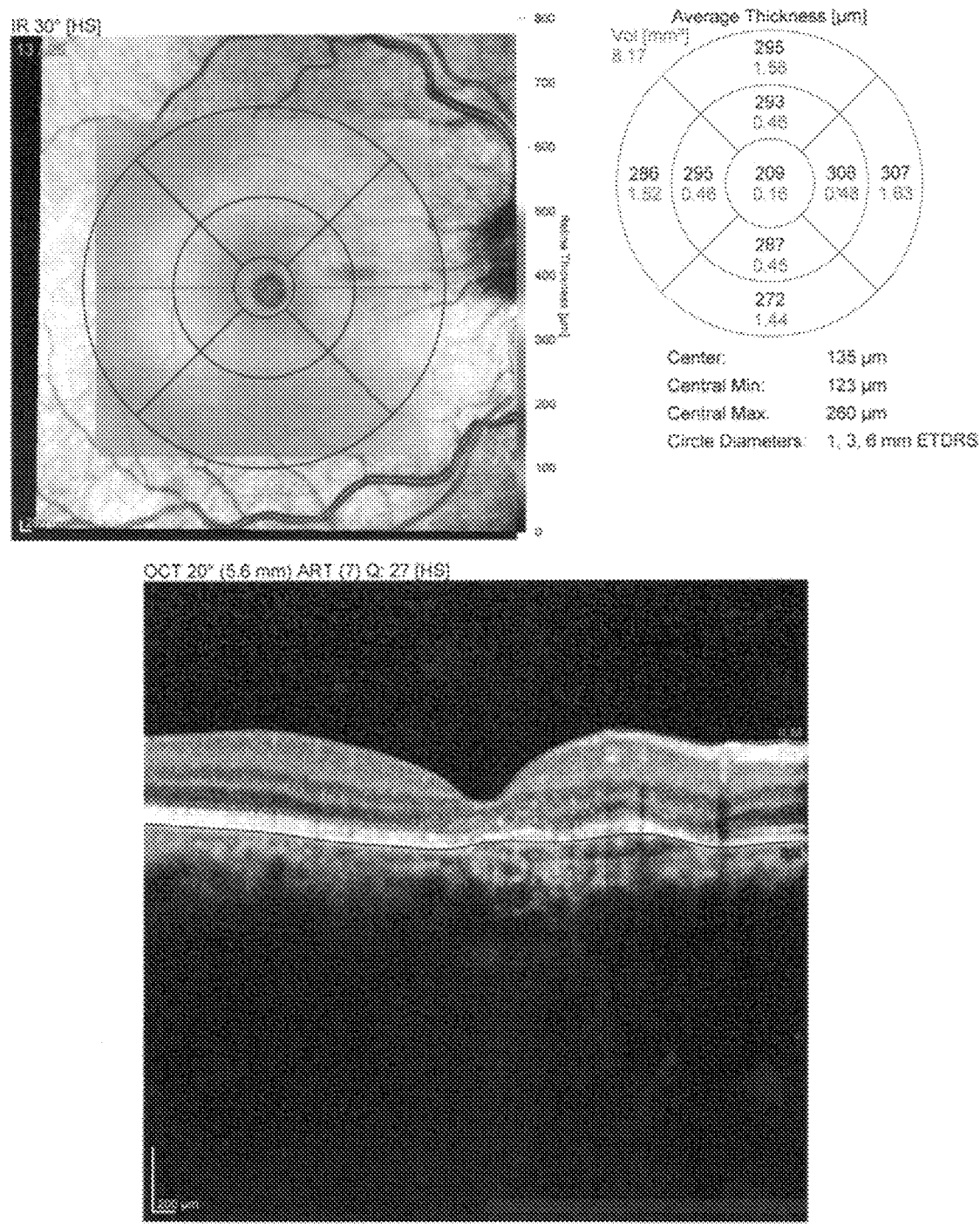
FIG. 11 is optical coherence tomography scans (OCT) of patient M.E., who has ARMD, after second round of treatment.

Successive OCT controls showed more improvement but no complete recovery (FIG. 07, 08, 09). Then we prescribe topically Salbutamol eye drops 0.1% (w/v), Ramiprilat eye drops 2% (W/v), Eplerenone eye drops 1% (w/v). N Acetyl DL Leucine eye drops 1% (w/v) association three times a day. Three months later, vision reached 10/10 fluoro-angiography revealed a decreased activity of the new vessel (FIG. 10). Follow-up OCT (FIG. 11) demonstrate a complete regression of macular thickening and recovery of foveal contour.

Figure 12:
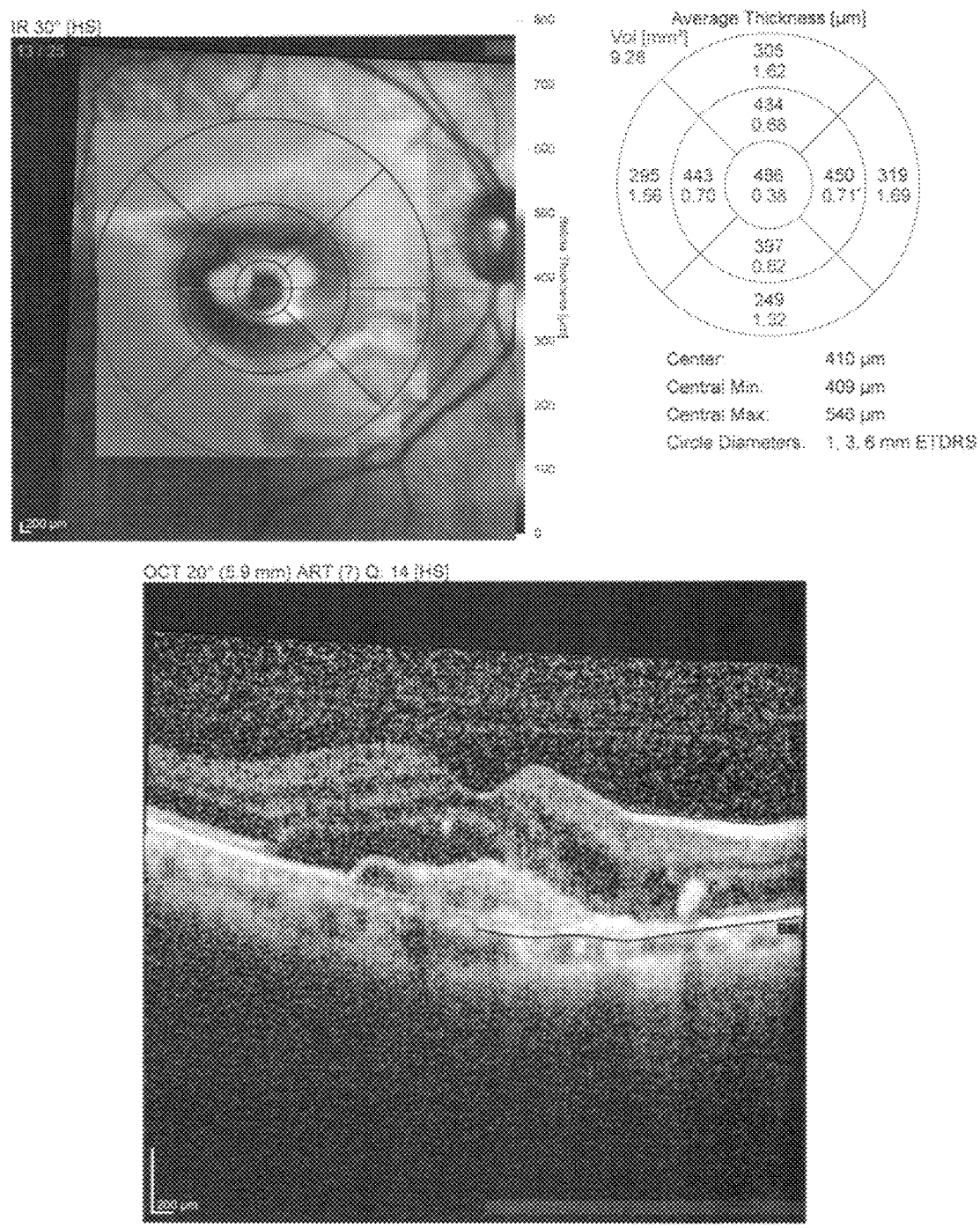
FIG. 12 is an optical coherence tomography scan (OCT) of patient K.A., who has ARMD, before first round of treatment.
Figure 13:
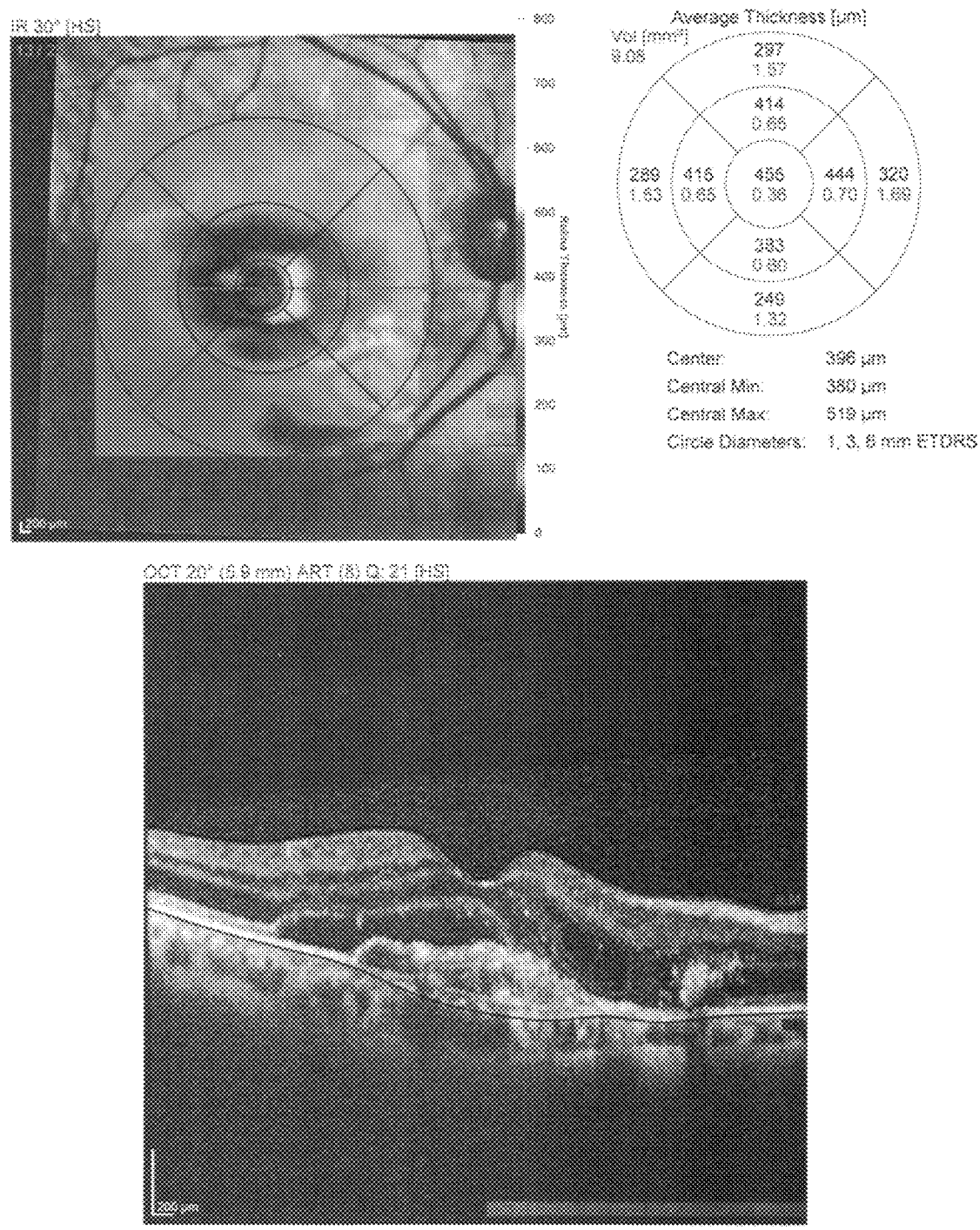
FIG. 13 is an optical coherence tomography scan (OCT) of patient K.A., who has ARMD, after first round of treatment

Patient K.A presented with a six months history of decreased vision in the right eye. An OCT exam revealed a macular thickening and a pigmentary epithelium detachment (FIG. 12).

He was treated with Salbutamol eye drops 0.1% (w/v). Three months later visual acuity improved. A follow-up OCT scan demonstrates an incomplete regression of macular thickening (FIG. β).

Figure 14:
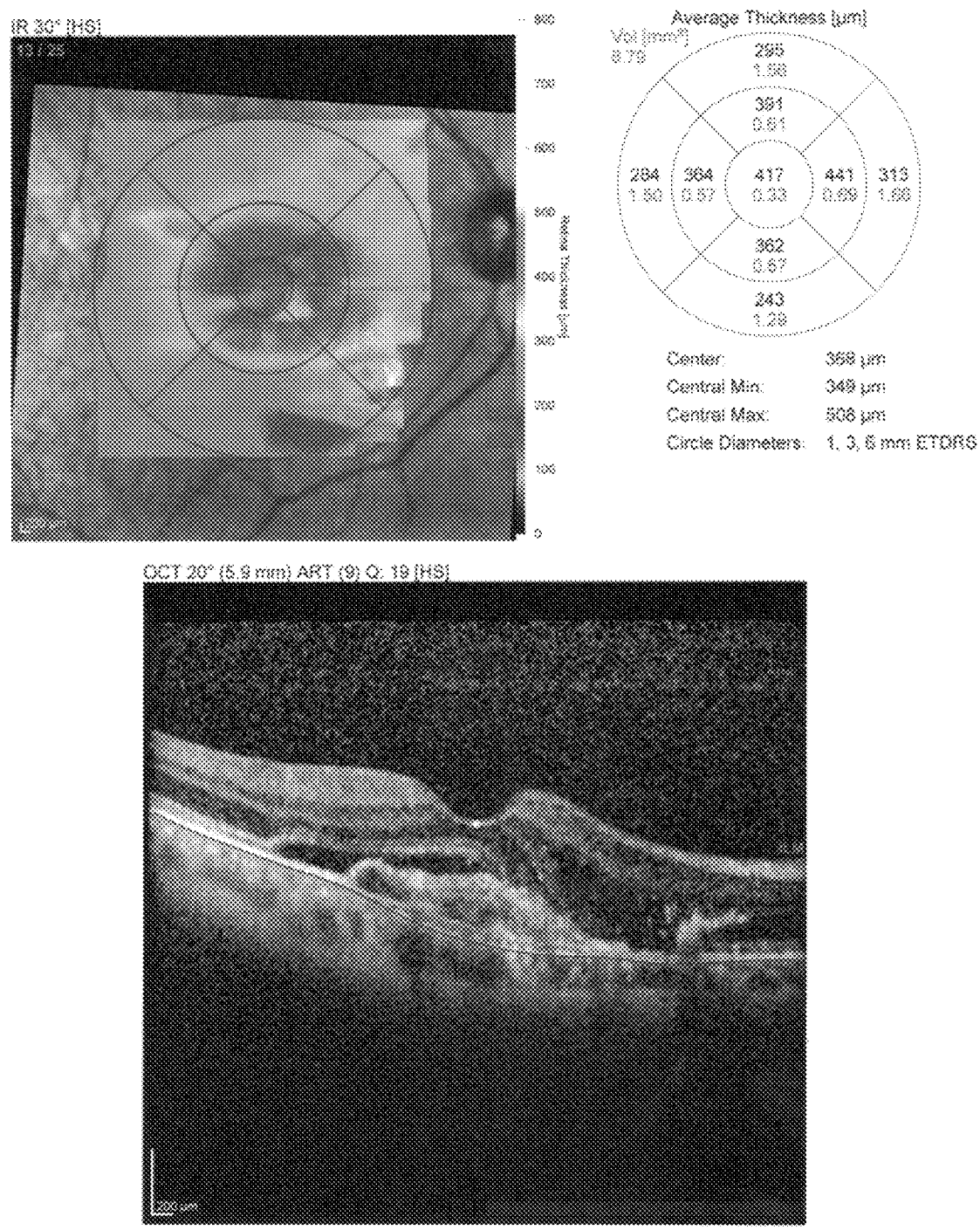
FIG. 14 is an optical coherence tomography scan (OCT) of patient K.A., who has ARMD, after second round of treatment.

Then he was given three times a day Salbutamol eye drops 0.1% (w/v), Ramiprilat eye drops 2% (w/v), Eplerenone eye drops 1% (w/v), N Acetyl DL Leucine eye drops 1% (w/v) association and he improved, visual acuity increased (4/10), follow-up OCT (FIG. 14) demonstrated more regression of macular thickening.

4) Central Serous Chorioretinopathy (CSCR)

CSCR is when fluid builds up under the retina. This can distort vision. The fluid leakage comes from a layer of tissue under the retina, called the choroid. There is another layer of cells called the retinal pigment epithelium (RPE). When the RPE doesn't work as it should, fluid builds up under the RPE. As a result, a small detachment forms under the retina, causing vision to become distorted.

Central serous chorioretinopathy usually affects just one eye at a time, but both eyes can be affected at the same time 07 patients suffering from CSCR were treated by: Salbutamol eye drops 0.1% (w/v) and Ramiprilat eye drops 2% (w/v) and Eplerenone eye drops 1% (w/v) and N Acetyl DL Leucine eye drops 1% (w/v). Three months later they noticed an improvement in visual acuity and OCT.

Figure 15:
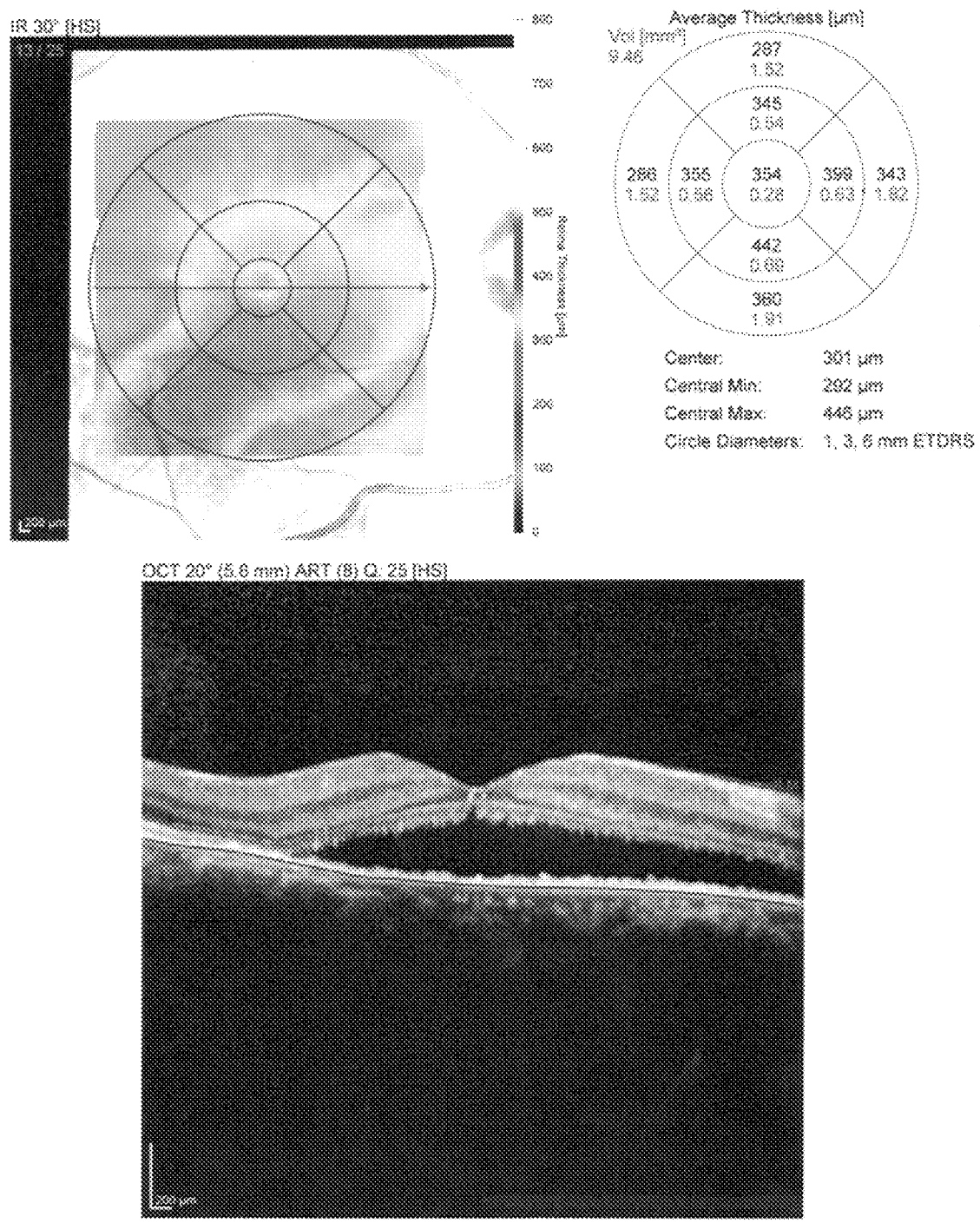
FIG. 15 is an optical coherence tomography scan (OCT) of patient B.S., who has CSCR, before treatment.

Patient B.S presented with chronic bilateral CSCR. Visual acuity respectively 1/10 in the right eye and 1/20 in the left eye, an OCT exam (FIG. 15) revealed a macular serous retinal detachment more important in the right eye. He received topically quadritherapy consisting of three times a day Salbutamol eye drops 0.1% (w/v) and Ramiprilat eye drops 2% (w/v) and Eplerenone eye drops 1% (w/v) and N Acetyl DL Leucine eye drops 1% (w/v).

Figure 16:
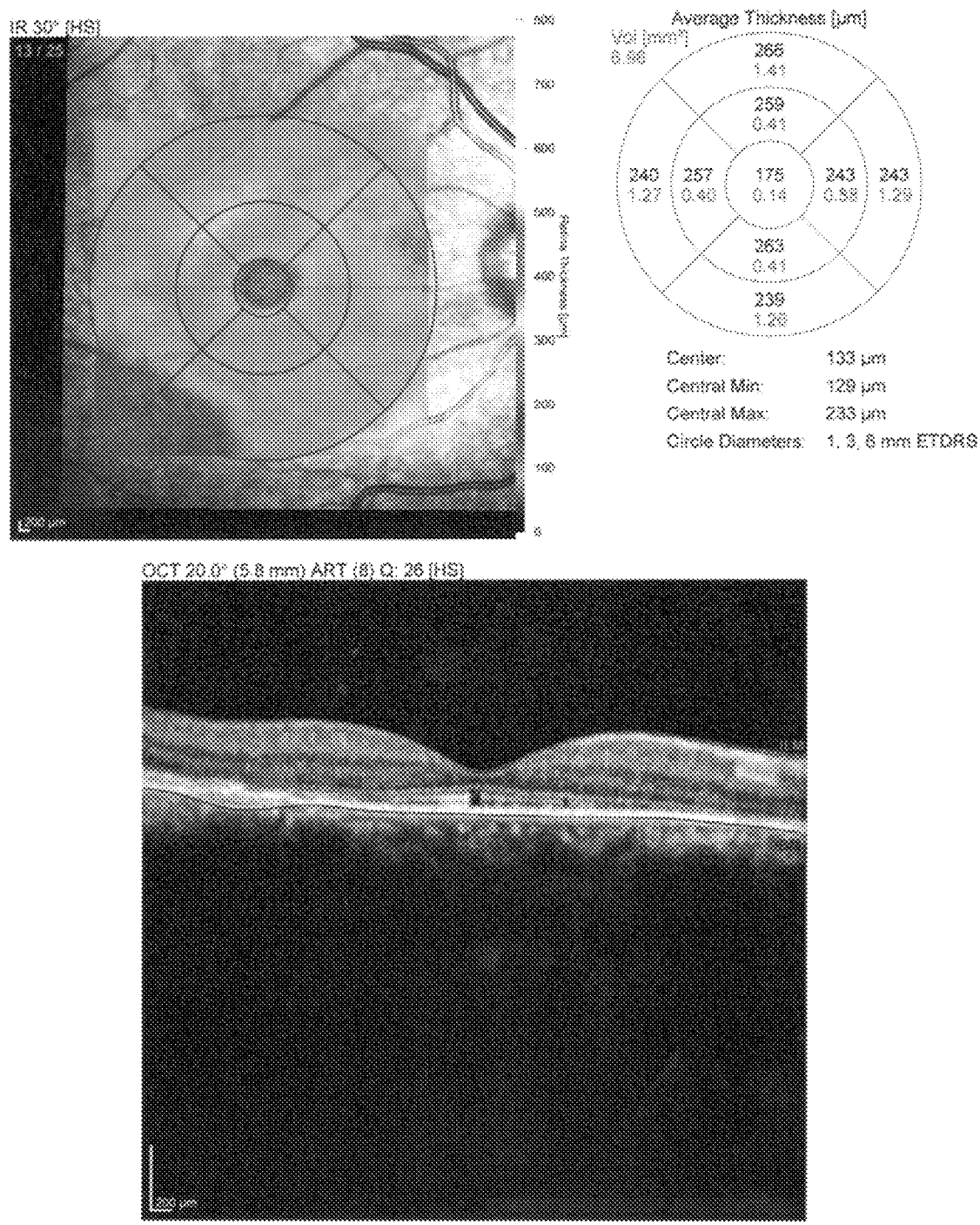
FIG. 16 is an optical coherence tomography scan (OCT) of patient B.S., who has CSCR, after treatment.

After two months, visual acuity in the right eye increased and reached 7/10. A follow-up OCT scan (FIG. 16) demonstrates a complete regression of the subretinal fluid and recovery of foveal contour.

Figure 17:
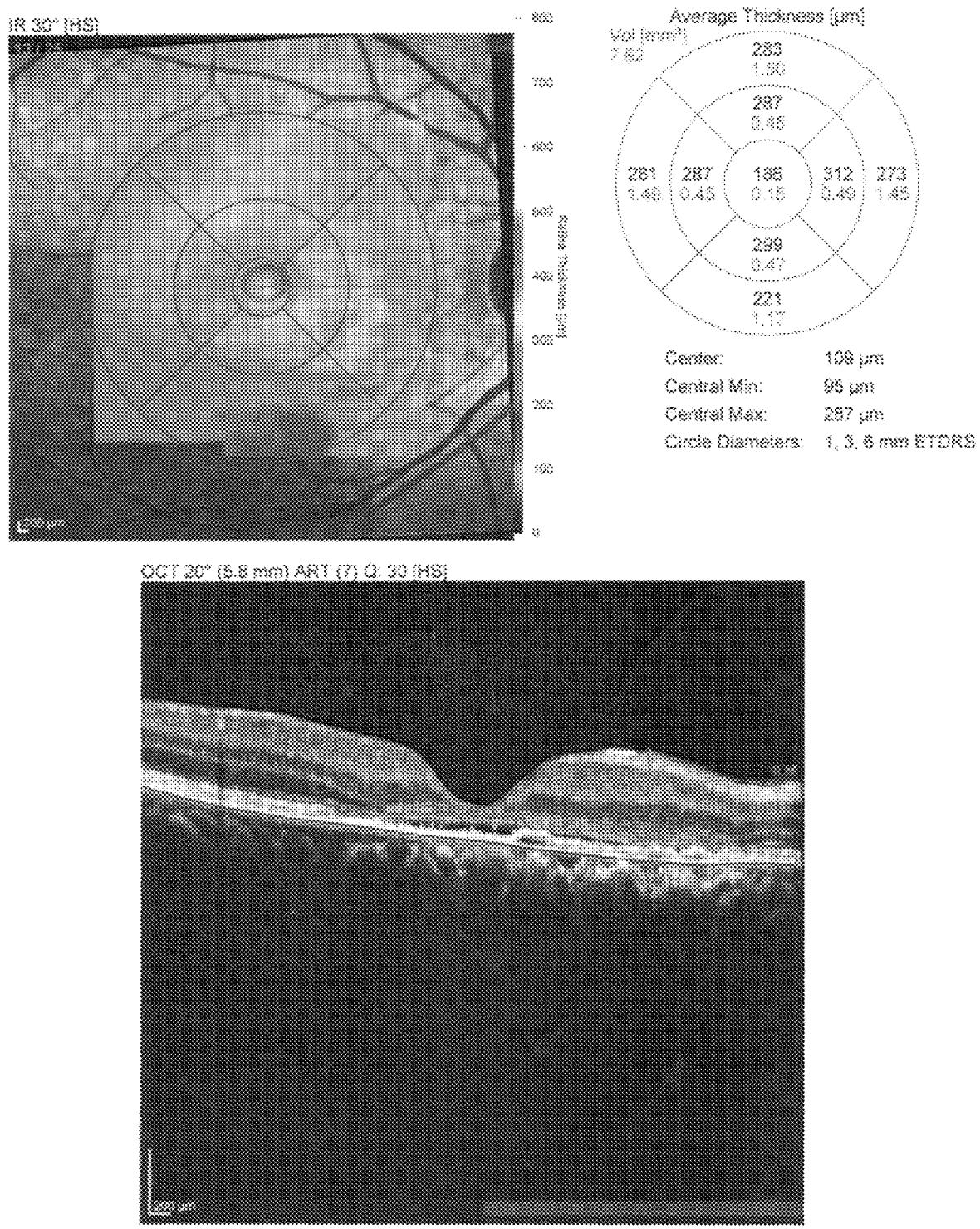
FIGS. 17 and 18 are optical coherence tomography scans (OCT) of patient E.A., who has CSCR, before treatment.
Figure 18:
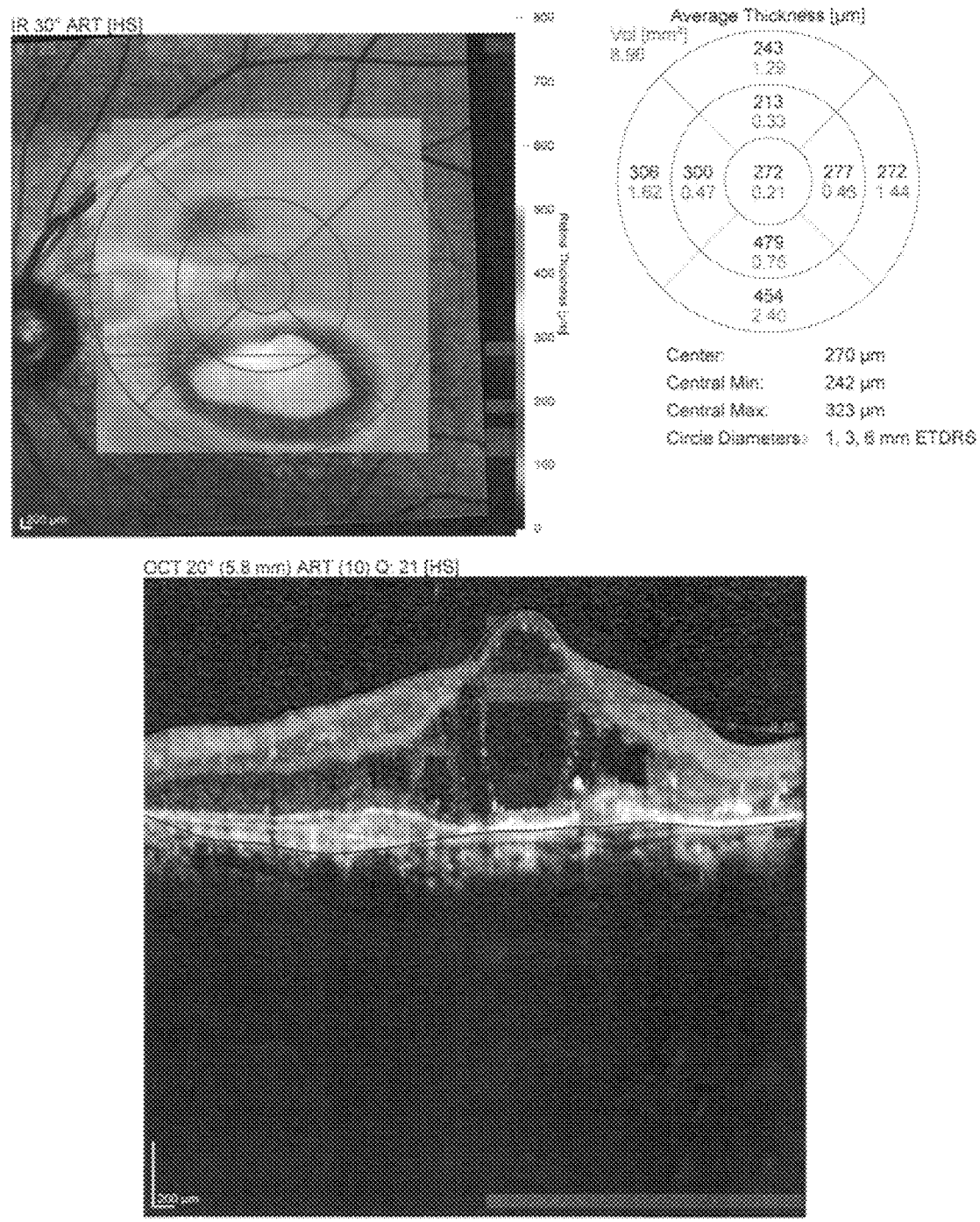

Patient E.A presented with chronic bilateral CSCR. Visual acuity respectively 2/10 in the right eye and 1/20 in the left eye, an OCT exam (FIG. 17, 18) revealed a macular serous retinal detachment more important in the left eye. He received topically quadritherapy consisting of three times a day Salbutamol eye drops 0.1% (w/v) and Ramiprilat eye drops 2% (w/v) and Eplerenone eye drops 1% (w/v) and N Acetyl DL Leucine eye drops 1% (w/v).

Figure 19:
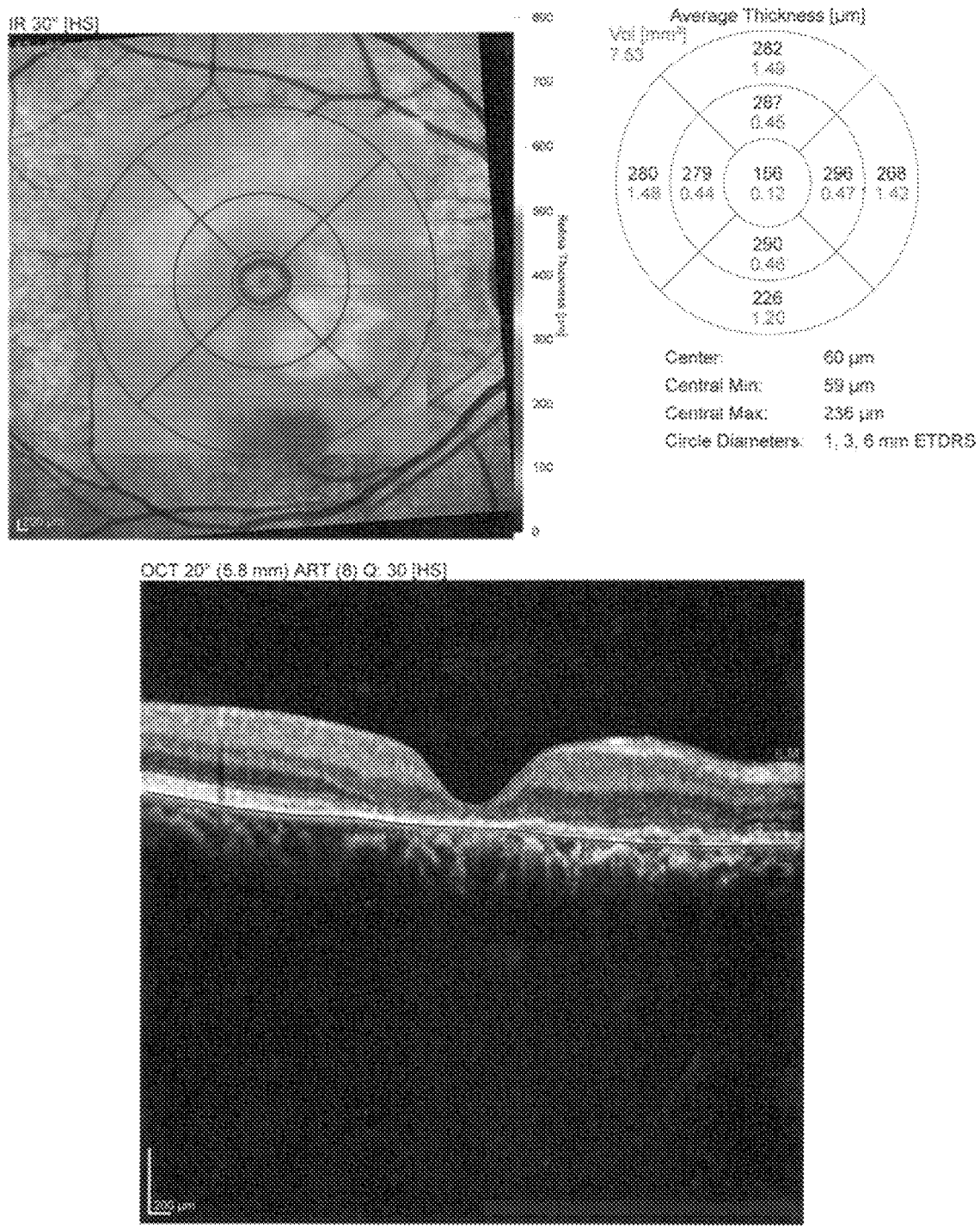
FIGS. 19 and 20 are optical coherence tomography scans (OCT) of patient E.A., who has CSCR, after treatment.
Figure 20:
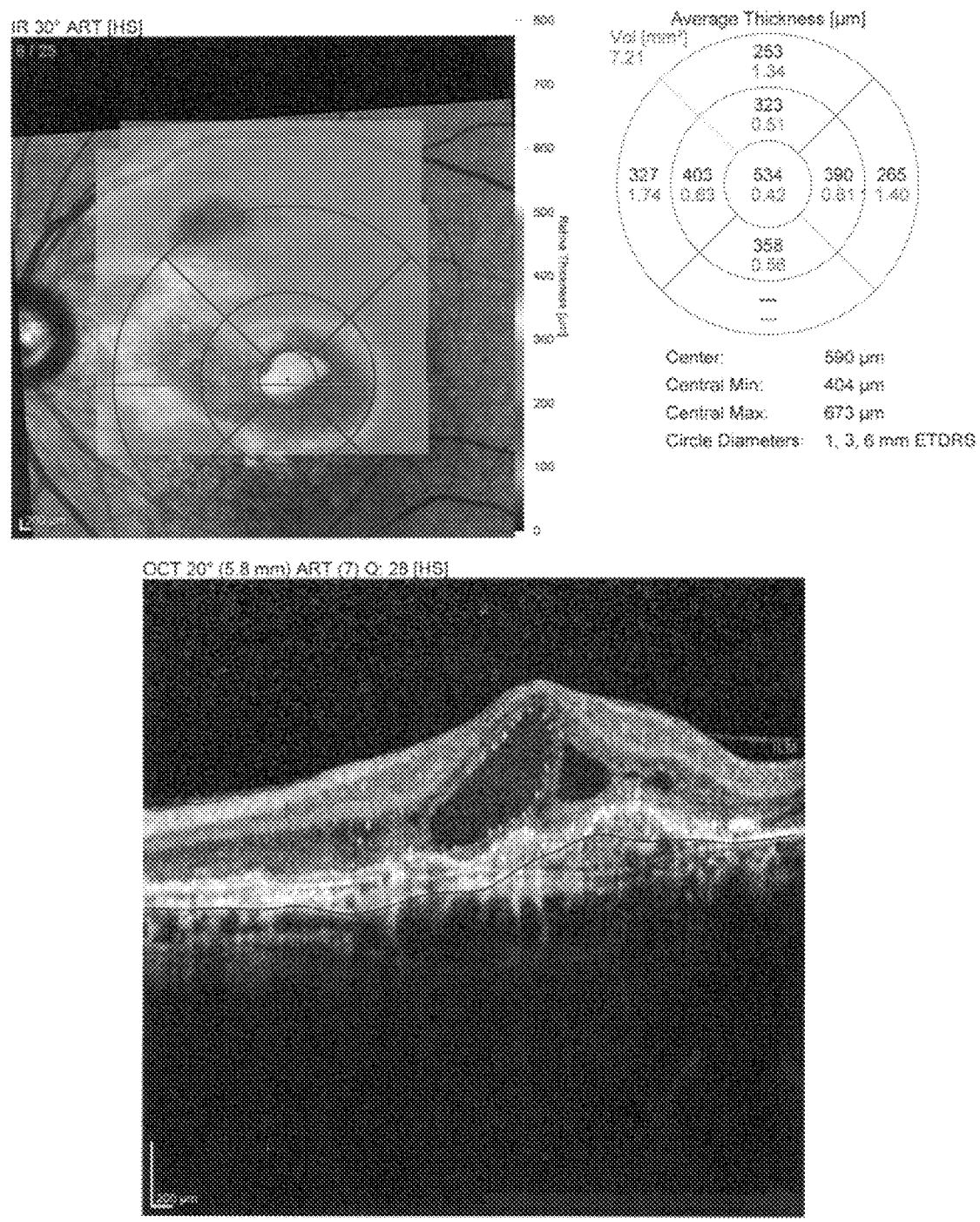

After three months, visual acuity in the right eye increased and reached 5-6/10. A follow-up OCT scan (FIG. 19) demonstrates a complete regression of the subretinal fluid in the right eye and incomplete in the left eye (FIG. 20) and recovery of foveal contour.

5) Uveitis, Optic Neuritis:

Uveitis is the inflammation of the uvea, the pigmented layer that lies between the inner retina and the outer fibrous layer composed of the sclera and cornea. The uvea consists of the middle layer of pigmented vascular structures of the eye and includes the iris, ciliary body, and choroid. Uveitis is an ophthalmic emergency and requires a thorough examination by an optometrist or ophthalmologist and urgent treatment to control the inflammation.

Uveitis is classified anatomically into anterior, intermediate, posterior, and panuveitic forms—based on the part of the eye primarily affected. Prior to the twentieth century, uveitis was typically referred to in English as "ophthalmia."

Anterior uveitis includes iridocyclitis and iritis. Iritis is the inflammation of the anterior chamber and iris. Iridocyclitis presents the same symptoms as iritis, but also includes inflammation in the ciliary body. [3] Anywhere from two-thirds to 90% of uveitis cases are anterior in location. This condition can occur as a single episode and subside with proper treatment or may take on a recurrent or chronic nature.

Intermediate uveitis also known as pars planitis, consists of vitritis—which is inflammation of cells in the vitreous cavity, sometimes with snowbanking, or deposition of inflammatory material on the pars plana. There are also "snowballs," which are inflammatory cells in the vitreous.

Posterior uveitis or chorioretinitis is the inflammation of the retina and choroid.

Pan-uveitis is the inflammation of all layers of the uvea.

Symptoms and Signs:
Anterior Uveitis:
  Burning of the eye
  Redness of the eye
  Blurred vision
  Photophobia or sensitivity to light
  Irregular pupil
  Blacked out sclera
  Floaters, which are dark spots that float in the visual field
  Headaches
  Signs of anterior uveitis include dilated ciliary vessels, presence of cells and flare in the anterior chamber, and keratic precipitates ("KP") on the posterior surface of the cornea. In severe inflammation there may be evidence of a hypopyon. Old episodes of uveitis are identified by pigment deposits on lens, KPs, and festooned pupil on dilation of pupil.
  Busacca nodules, inflammatory nodules located on the surface of the iris in granulomatous forms of anterior uveitis such as Fuchs heterochromic iridocyclitis (FHI).
  Synechia
Intermediate Uveitis:
Most Common:
  Floaters
  Blurred vision
  Intermediate uveitis normally only affects one eye. Less common is the presence of pain and photophobia.
Posterior Uveitis:
  Inflammation in the back of the eye is commonly characterized by:
  Floaters
  Blurred vision
  Photopsia or seeing flashing lights In 10 cases of uveitis; salbutamol alone or associated with one or more of these: non-steroidal anti inflammatory drugs, angiotensin converting enzyme inhibitors, aldosterone receptors antagonist, β1 blocker, anhydrase carbonic inhibitor, magnesium, corticosteroids and serrapeptase reduced inflammatory disorders.

Figure 21:
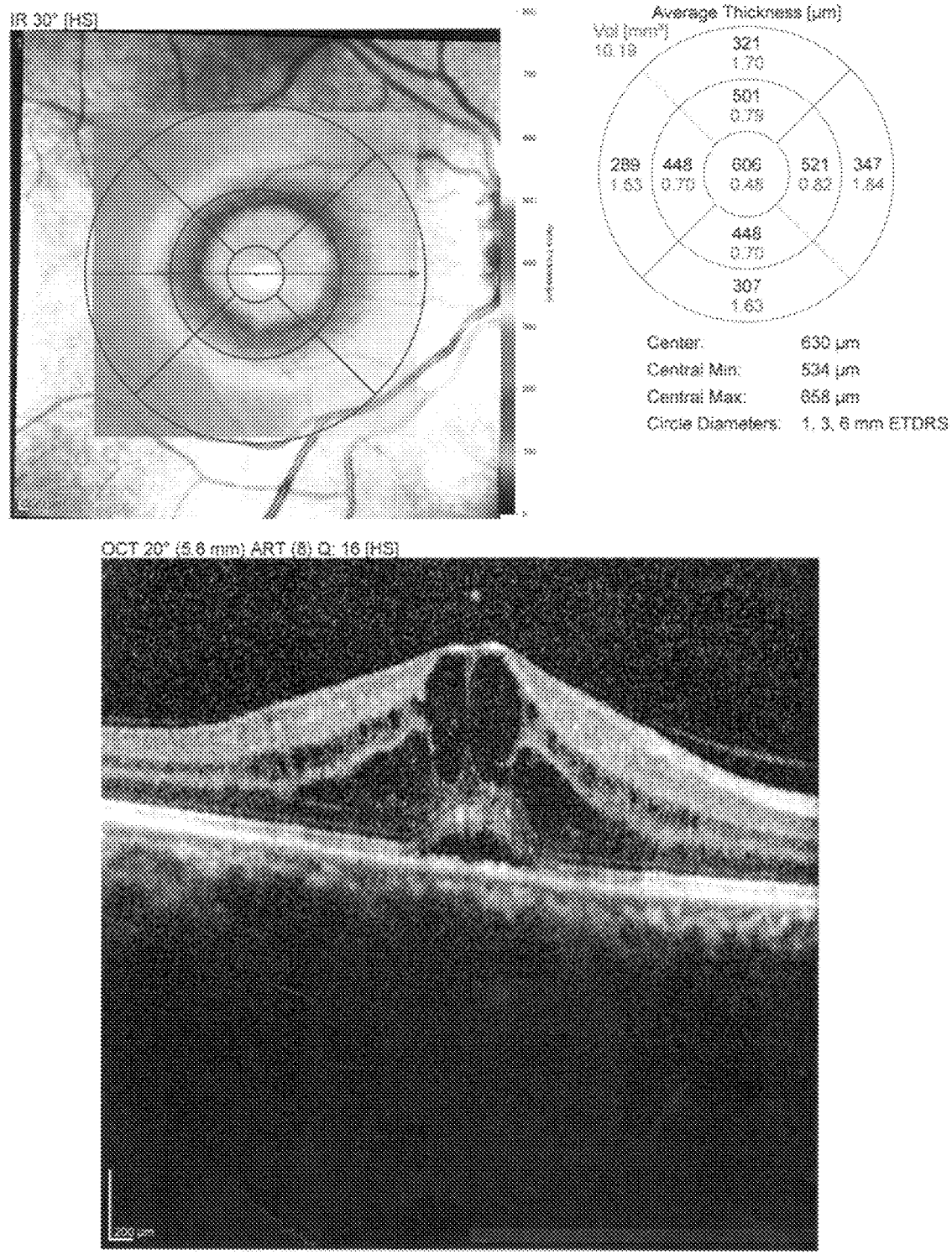
FIG. 21 and FIG. 22 are optical coherence tomography scans (OCT) of patient S.M., who has uveitis, before treatment.
Figure 22:
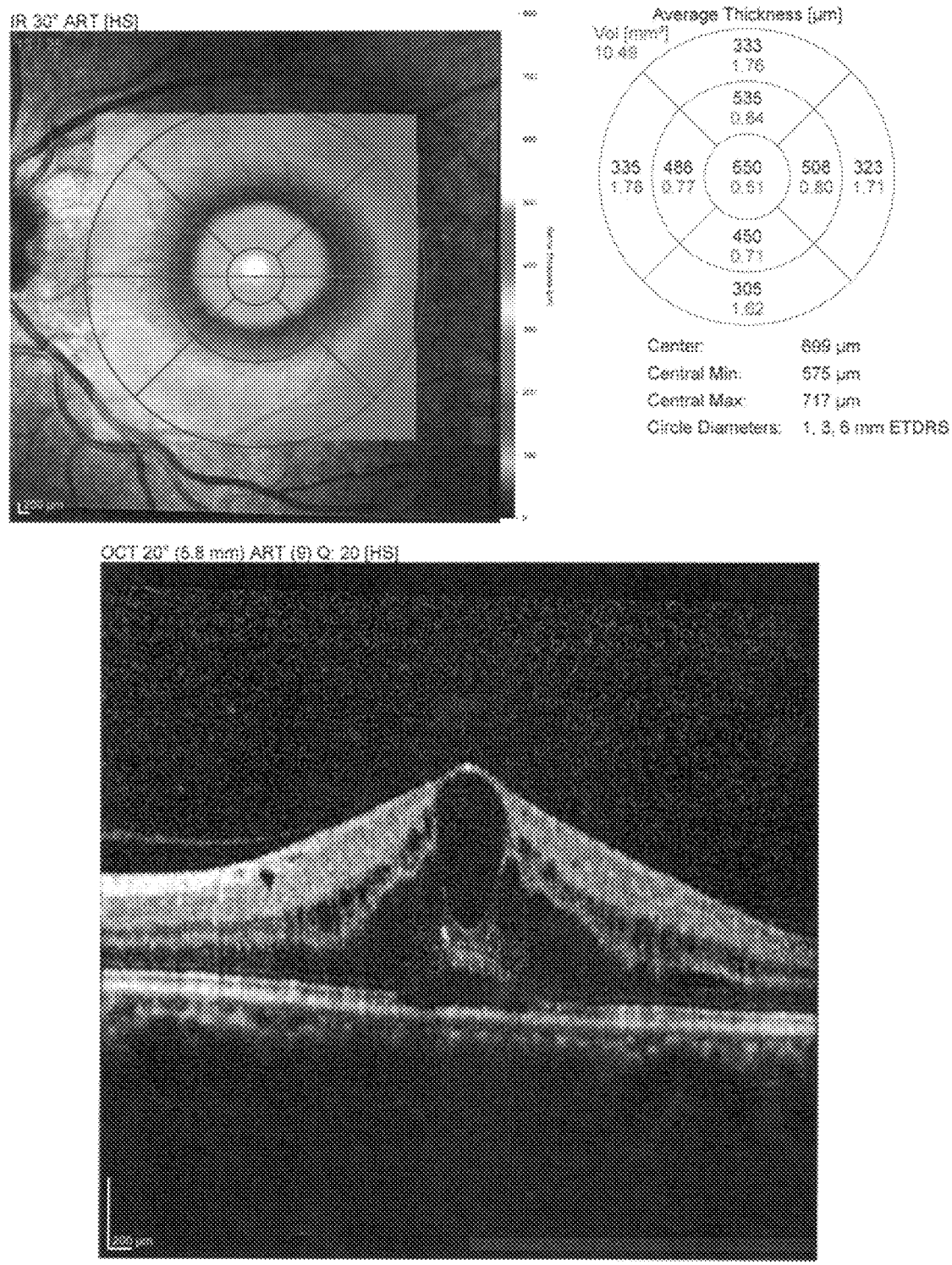

One of them S.M, presented with bilateral uveitis including macular oedema and reduced visual acuity. An OCT exam (OD FIG. 21, OS FIG. 22) revealed a macular thickening in both eyes, she received a local quadritherapy treatment based on Salbutamol eye drops 0.1% (w/v), Ramiprilat eye drops 2% (w/v), Eplerenone eye drops 1% (w/v) and N Acetyl DL Leucine eye drops 1% (w/v).

Figure 23:
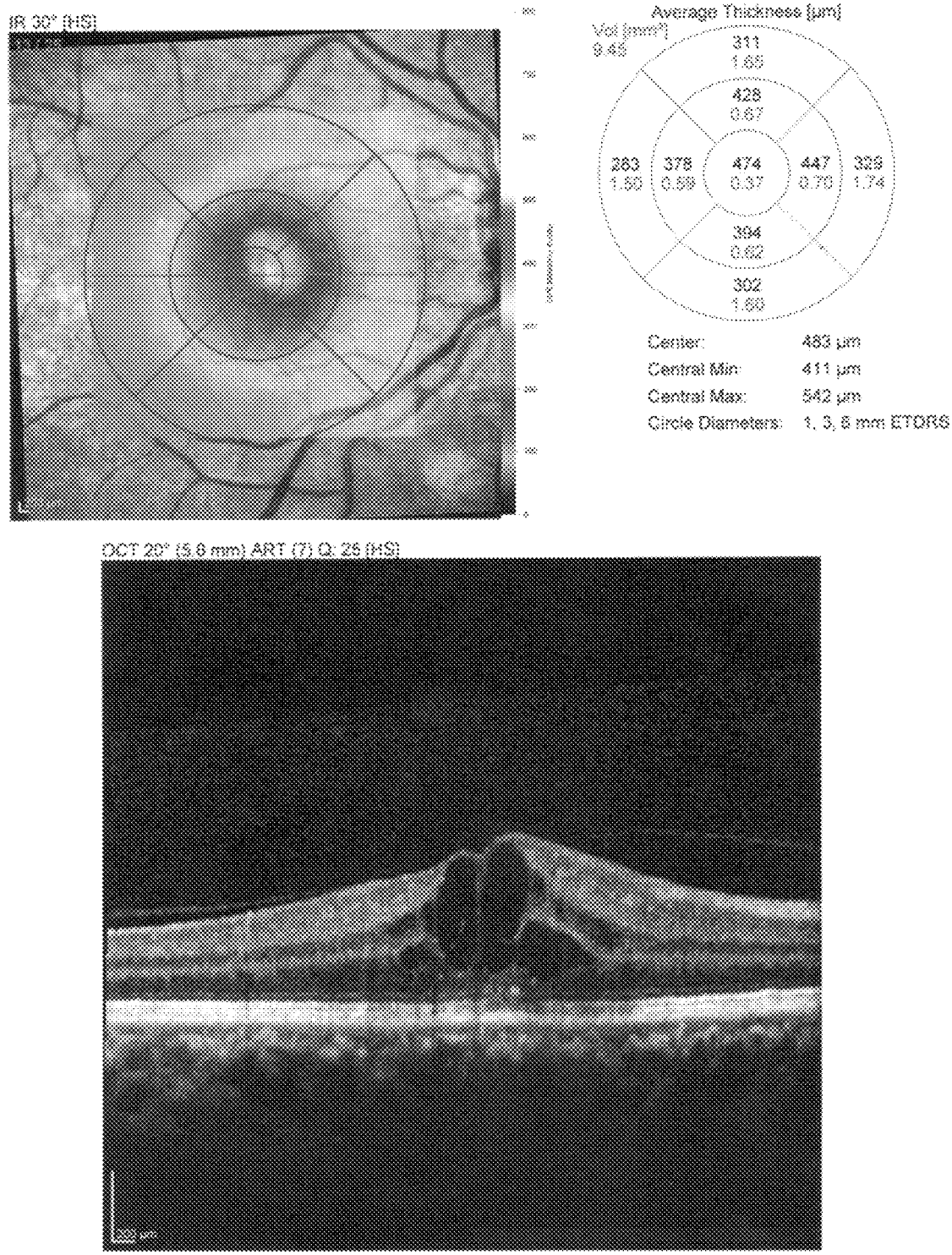
FIG. 23 and FIG. 24 are optical coherence tomography scans (OCT) of patient S.M., who has uveitis, after 1 month treatment.
Figure 24:
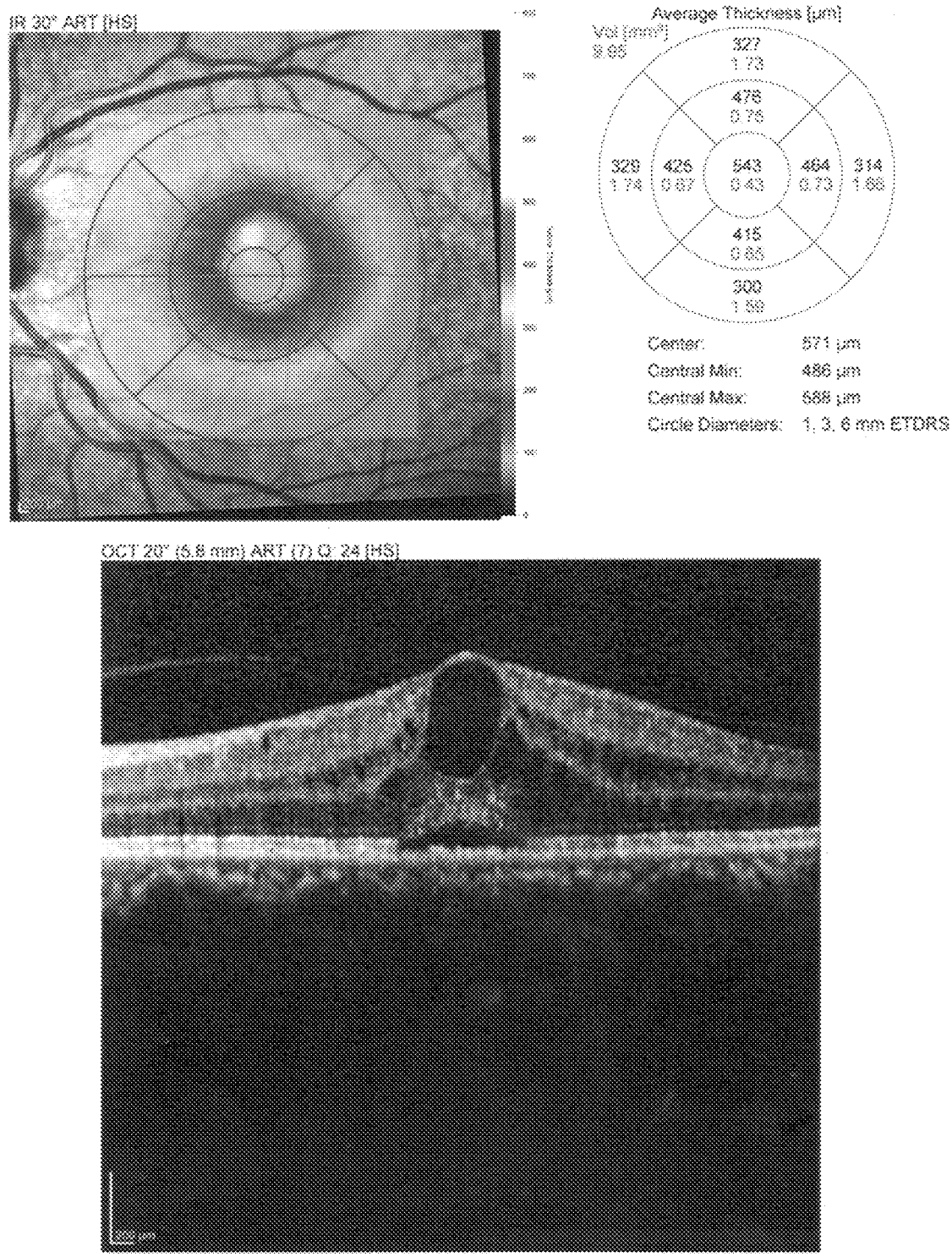

One month later, visual acuity improved. We noted an incomplete regression of macular thickening (OD FIG. 23, OS FIG. 24).

Figure 25:
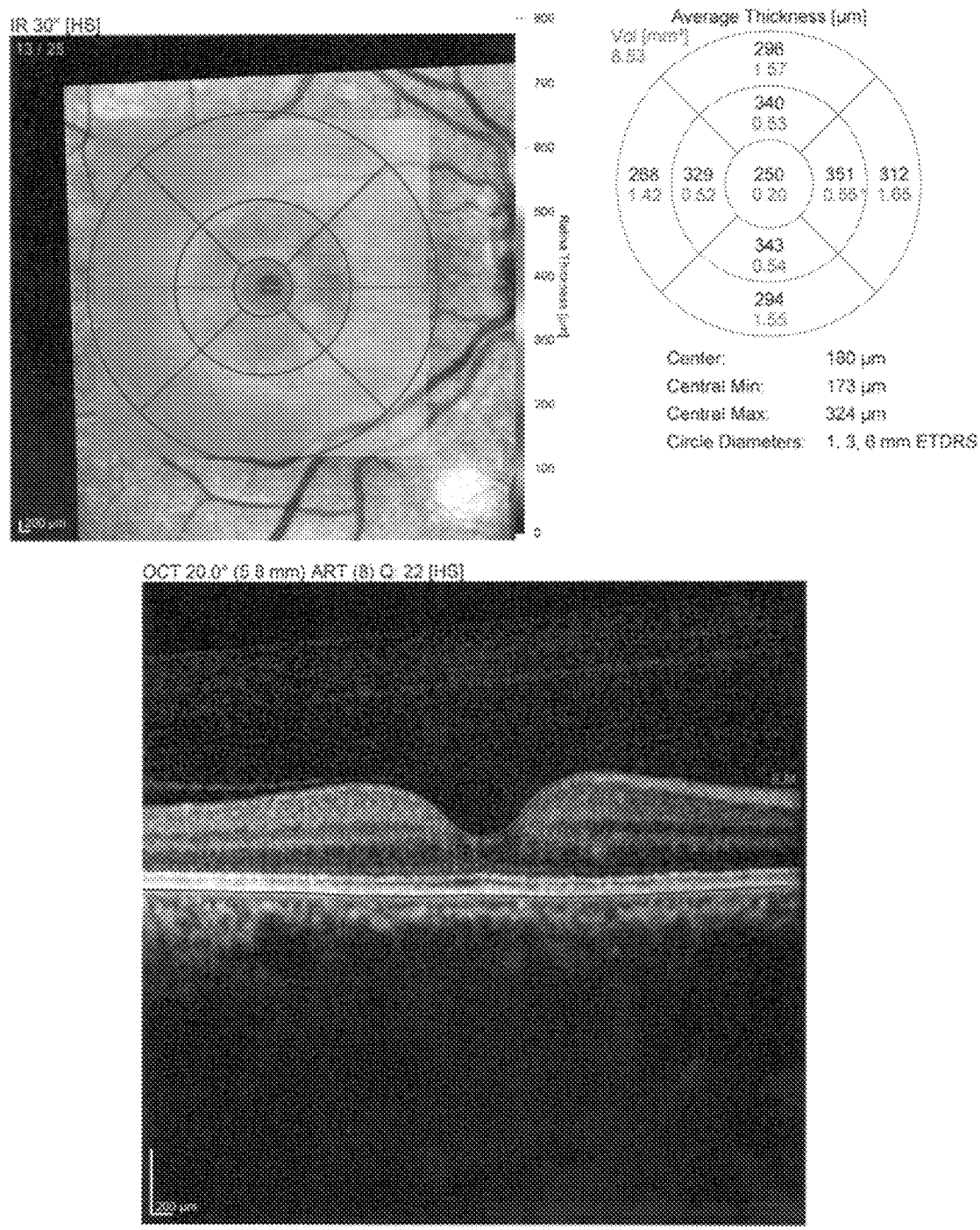
FIG. 25 and FIG. 26 are optical coherence tomography scans (OCT) of patient S.M., who has uveitis, after 3 months treatment.
Figure 26:
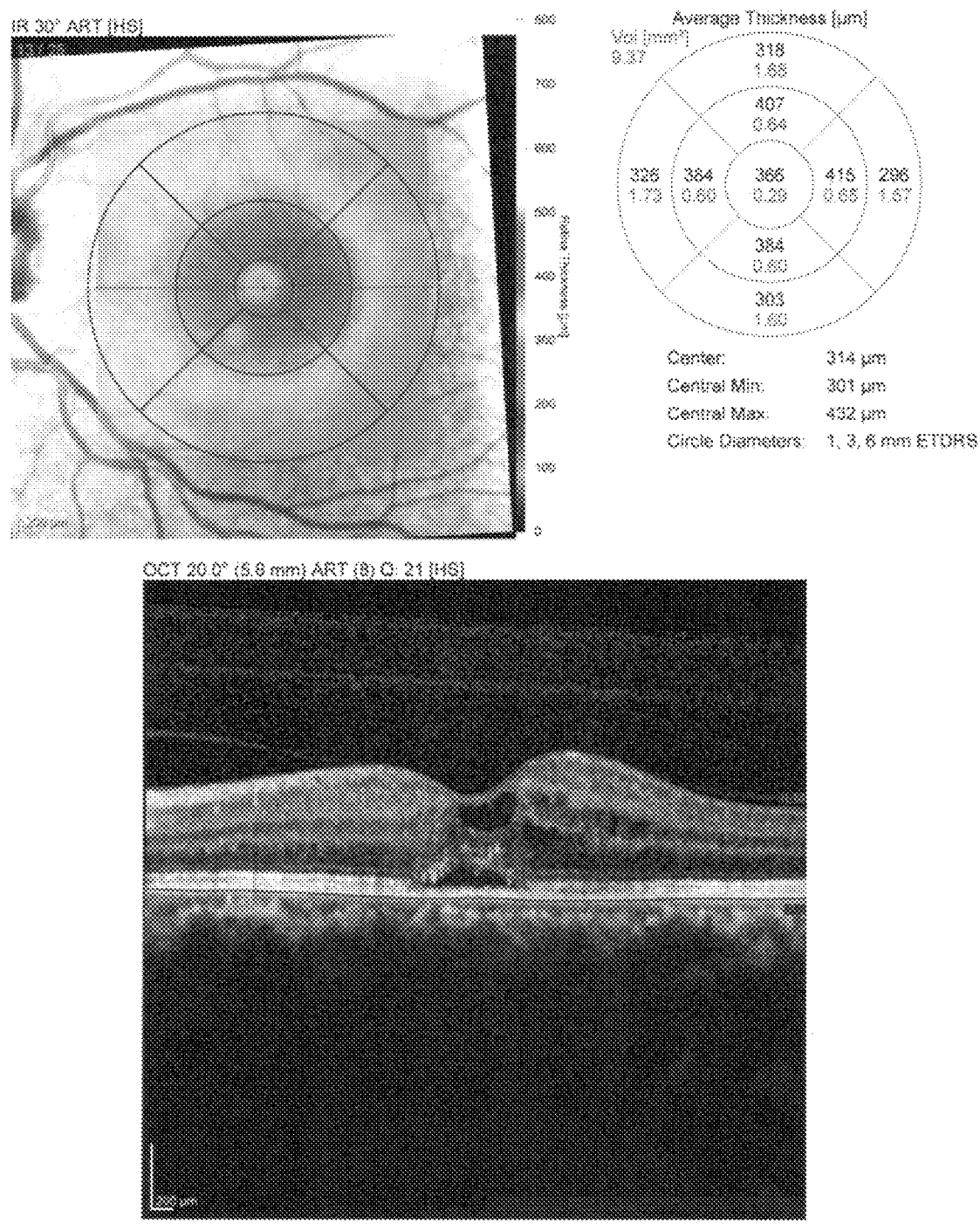

Three month later, visual acuity was 10/10 in both eyes and regression of macular oedema was complete (OD FIG. 25, OS FIG. 26). Inflammation has regressed completely.

6) Glaucoma Neuropathy or Glaucoma

Glaucoma is a disease that damages your eye's optic nerve. It usually happens when fluid builds up in the front part of your eye. That extra fluid increases the pressure in your eye, damaging the optic nerve. Glaucoma is a leading cause of blindness for people over 60 years old. But blindness from glaucoma can often be prevented with early treatment.

There are two major types of glaucoma:
Primary Open-Angle Glaucoma

This is the most common type of glaucoma. It happens gradually, where the eye does not drain fluid as well as it should (like a clogged drain). As a result, eye pressure builds and starts to damage the optic nerve. This type of glaucoma is painless and causes no vision changes at first.

Some people can have optic nerves that are sensitive to normal eye pressure. This means their risk of getting glaucoma is higher than normal. Regular eye exams are important to find early signs of damage to their optic nerve.

Angle-closure glaucoma (also called "closed-angle glaucoma" or "narrow-angle glaucoma")

This type happens when someone's iris is very close to the drainage angle in their eye. The iris can end up blocking the drainage angle. You can think of it like a piece of paper sliding over a sink drain. When the drainage angle gets completely blocked, eye pressure rises very quickly. This is called an acute attack. It is a true eye emergency, and you should call your ophthalmologist right away or you might go blind.

Here are the signs of an acute angle-closure glaucoma attack:

Your vision is suddenly blurry
You have severe eye pain
You have a headache
You feel sick to your stomach (nausea)
You throw up (vomit)
You see rainbow-colored rings or halos around lights Many people with angle-closure glaucoma develop it slowly. This is called chronic angle-closure glaucoma. There are no symptoms at first, so they don't know they have it until the damage is severe or they have an attack.

Angle-closure glaucoma can cause blindness if not treated right away.

Patients with known glaucoma experienced a decrease in their ocular tension, and an improvement of their visual acuity and visual field once they are treated with Salbutamol or salbutamol associated with one or more of these: N Acetyl DL Leucine, glucose, magnesium, aldosterone receptor antagonist (eplerenone), angiotensin converting enzyme inhibitor (Ramiprilat), β1 blocker and anhydrase carbonic inhibitor.

7) Hereditary Dystrophy of the Retina:

Pigmentosa retinitis:

Retinitis pigmentosa (RP) is an inherited, degenerative eye disease that causes severe vision impairment due to the progressive degeneration of the rodphotoreceptor cells in the retina. This form of retinal dystrophy manifests initial symptoms independent of age; thus, RP diagnosis occurs anywhere from early infancy to late adulthood. Patients in the early stages of RP first notice compromised peripheral and dim light vision due to the decline of the rod photoreceptors. The progressive rod degeneration is later followed by abnormalities in the adjacent retinal pigment epithelium (RPE) and the deterioration of cone photoreceptor cells. As peripheral vision becomes increasingly compromised, patients experience progressive "tunnel vision" and eventual blindness. Affected individuals may additionally experience defective light-dark adaptations, nyctalopia (night blindness), and the accumulation of bone spicules in the fundus.

The initial retinal degenerative symptoms of Retinitis Pigmentosa are characterized by decreased night vision (nyctalopia) and the loss of the mid-peripheral visual field. The rod photoreceptor cells, which are responsible for low-light vision and are orientated in the retinal periphery, are the retinal processes affected first during non-syndromic forms of this disease. Visual decline progresses relatively quickly to the far peripheral field, eventually extending into the central visual field as tunnel vision increases. Visual acuity and color vision can become compromised due to accompanying abnormalities in the cone photoreceptor cells, which are responsible for color vision, visual acuity, and sight in the central visual field. The progression of disease symptoms occurs in a symmetrical manner, with both the left and right eyes experiencing symptoms at a similar rate.

A variety of indirect symptoms characterizes Retinitis Pigmentosa along with the direct effects of the initial rod photoreceptor degeneration and later cone photoreceptor decline. Phenomena such as photophobia, which describes the event in which light is perceived as an intense glare, and photopsia, the presence of blinking or shimmering lights within the visual field, often manifest during the later stages of RP. Findings related to RP have often been characterized in the fundus of the eye as the Ophthalamic triad. This includes the development of a mottled appearance of the retinal pigment epithelium (RPE) caused by bone spicule formation, a waxy appearance of the optic nerve, and the attentuation of blood vessels in the retina.

Non-syndromic RP usually presents a variety of the following symptoms:

Night blindness or nyctalopia;
Tunnel vision (due to loss of peripheral vision);
Latticework vision;
Photopsia (blinking/shimmering lights);
Photophobia (Aversion to glare);
Development of bone spicules in the fundus;
Slow adjustment from dark to light environments and vice versa;
Blurring of vision;
Poor color separation;
Loss of central vision;
Eventual blindness Salbutamol was used and induced an improvement of visual function.

9 patients were treated. All of them noticed an improvement of their visual acuity and their visual field.

Staroardt's Disease

Stargardt disease, or fundus flavimaculatus, is the most frequent form of inherited juvenile macular degeneration. Stargardt causes progressive vision loss usually to the point of legal blindness. Several genes are associated with the disorder. Symptoms, mainly central vision loss, typically develop before age 20 (median age of onset: ~17 years old), and also include wavy vision, blind spots, blurriness, impaired color vision, and difficulty adapting to dim lighting (dark adaptation delays).

Stargardt is often used to refer to any juvenile macular dystrophy; however, it properly refers to atrophic macular dystrophy with yellow, poorly-defined flecks surrounding the macula in the retinal pigment epithelium.

Patients with Stargardt disease usually develop symptoms in the mid-first to the late second decade of life, with age of onset which can be as early as ~6 years of age. The main symptom of Stargardt disease is loss of visual acuity, uncorrectable with glasses, which progresses and frequently stabilizes between 20/200 and 20/400. Other symptoms include wavy vision, blind spots (scotomata), blurriness, impaired color vision, and difficulty adapting to dim lighting (delayed dark adaptation). The disease sometimes causes sensitivity to glare; overcast days offer some relief. Vision is most noticeably impaired when the macula (center of retina and focus of vision) is damaged, leaving peripheral vision more intact. Generally, vision loss starts within the first 20 years of life.

Examination with an ophthalmoscope shows few notable findings in the early stages of the disease. Eventually, however, an oval-shaped atrophy with a horizontal major axis appears in the retinal pigment epithelium, and has the appearance of beaten bronze, along with sparing of the area surrounding the optic disc (peripapillary sparing). Techniques such as fundus autofluorescence (FAF), Optical Coherence Tomography (OCT), or less frequently fluorescein angiography, can detect early signs before they are visible ophthalmoscopically.

8 patients treated with Salbutamol noticed an improvement of their visual acuity.

If we associate to Salbutamol one or more of these: N Acetyl DL Leucine, nitric monoxide donor (vitamin C, vitamin B9), Ramiprilat, and aldosterone receptor antagonist; improvement is noted.

8) Cataract:

Some improvement had been noticed under salbutamol.

9) Corneal Oedema:

10 patients improve their vision after Salbutamol treatment and the oedema decreased.

10) Age Related Physiological Vision Decline:

In many cases, Salbutamol improved visual function in the absence of any ocular pathology.

11) Dry Eye: is improved in 7 patients after Salbutamol eye drops treatment.

12) Allergic conjunctivitis and blepharitis: is improved in 5 patients after Salbutamol eye drops treatment.

13) Periretinal fibrosis: is reduced after Salbutamol treatment.

14) Vitreo Macular Traction:

Salbutamol seems to have a proteolytic activity. It promotes a vitreolysis inducing both synchesis and synerisis without adversely affecting the retina.

In many cases of proliferative diabetic retinopathy including fibrovascular proliferation, retinal detachment, vitreo macular traction, the intravitreal injection of Salbutamol led to induction of posterior vitreous detachment, easier peeling and removal of epiretinal fibrotic membrane and internal limiting membrane particularly in macular hole pathology.

15) Vitreous hemorrhage: in many cases it decreased after Salbutamol treatment.

The invention claimed is:

1. A method for treating diabetic retinopathy in a subject in need of such treatment, comprising administering to the subject salbutamol or a pharmaceutically acceptable salt thereof, angiotensin converting enzyme inhibitor(s) or pharmaceutically acceptable salt(s) thereof, aldosterone receptor antagonist(s) or pharmaceutically acceptable salt(s) thereof, and N-acetyl-DL-leucine or a pharmaceutically acceptable salt thereof.

2. The method according to claim 1, wherein salbutamol or a pharmaceutically acceptable salt thereof, angiotensin converting enzyme inhibitor(s) or pharmaceutically acceptable salt(s) thereof, aldosterone receptor antagonist(s) or pharmaceutically acceptable salt(s) thereof, and N-acetyl-DL-leucine or a pharmaceutically acceptable salt thereof are found within a single composition or several separate compositions, and when found within several separate compositions, said separate compositions are administered simultaneously or sequentially to the subject.

3. The method according to claim 2, wherein:
   (a) the angiotensin converting enzyme inhibitor is selected from the group consisting of: fosinopril, ramipril, captopril, trandolapril, moexipril, quinapril, enalapril, perindopril, benazepril, fosinoprilate, trandolaprilate, moexiprilate, ramiprilate, quinaprilate, enalaprilate, perindoprilate, benazeprilate, and mixtures thereof, and/or
   (b) the aldosterone receptor antagonist is eplerenone.

4. The method according to claim 1, comprising administering to the subject a composition comprising or consisting essentially of or consisting of salbutamol, ramiprilate, eplerenone, and N-acetyl-DL-leucine.

5. The method according to claim 1, wherein salbutamol or a pharmaceutically acceptable salt thereof, angiotensin converting enzyme inhibitor(s) or pharmaceutically acceptable salt(s) thereof, aldosterone receptor antagonist(s) or pharmaceutically acceptable salt(s) thereof, and N-acetyl-DL-leucine or a pharmaceutically acceptable salt thereof are administered to the subject orally, parenterally, intravenously, intravascularly, intramuscularly, transdermally, or topically.

6. The method according to claim 5, wherein salbutamol or a pharmaceutically acceptable salt thereof, angiotensin converting enzyme inhibitor(s) or pharmaceutically acceptable salt(s) thereof, aldosterone receptor antagonist(s) or pharmaceutically acceptable salt(s) thereof, and N-acetyl-DL-leucine or a pharmaceutically acceptable salt thereof are administered to the subject topically to the eye through eye drops or intraocular injection or intravitreal injection.

7. The method according to claim 1, wherein salbutamol or a pharmaceutically acceptable salt thereof, angiotensin converting enzyme inhibitor(s) or pharmaceutically acceptable salt(s) thereof, aldosterone receptor antagonist(s) or pharmaceutically acceptable salt(s) thereof, and N-acetyl-DL-leucine or a pharmaceutically acceptable salt thereof are in the form of a solution, an ophthalmic solution or eye drops, a lotion, drops, a cream or an ointment.

8. The method according to claim 1, wherein:
   salbutamol is administered topically in a concentration ranging from 0.05 to 0.2% (w/v), and
   the angiotensin converting enzyme inhibitor is ramiprilate that is administered topically in a concentration ranging from 0.5 to 5% (w/v), and
   the aldosterone receptor antagonist is eplerenone that is administered topically in a concentration ranging from 0.5 to 5% (w/v), and
   N-acetyl-DL-leucine is administered topically in a concentration ranging from 0.5 to 5% (w/v).

9. The method according to claim 1, wherein salbutamol or a pharmaceutically acceptable salt thereof, angiotensin converting enzyme inhibitor(s) or pharmaceutically acceptable salt(s) thereof, aldosterone receptor antagonist(s) or pharmaceutically acceptable salt(s) thereof, and N-acetyl-DL-leucine or a pharmaceutically acceptable salt thereof are administered:
   (a), one, two, three, or four times a day, and/or
   (b), over a period of time of 1, 2 or 3 months.

10. The method according to claim 1, wherein salbutamol, the angiotensin converting enzyme inhibitor that is ramiprilate, the aldosterone receptor that is eplerenone, and N-acetyl-DL-leucine are simultaneously or sequentially administered topically to a subject, one, two, three, or four times a day, to the subject over a period of time of 1, 2, or 3 months.

11. The method of claim 2, wherein the single composition or the several separate compositions further comprise pharmaceutically acceptable additive(s), diluent(s) or vehicle(s) or carrier(s).

12. The method according to claim 8, wherein
   salbutamol is administered topically at a concentration of 0.1% (w/v), and
   ramiprilate is administered topically at a concentration of 2% (w/v), and
   eplerenone is administered topically at a concentration of 1% (w/v), and
   N-acetyl-DL-leucine is administered topically at a concentration of 1% (w/v).

13. The method according to claim 8, wherein
   salbutamol is administered topically in a concentration ranging from 0.05 to 1% (w/v), and
   ramiprilate is administered topically in a concentration ranging from 0.5 to 3% (w/v), and eplerenone is administered topically in a concentration ranging from 0.5 to 3% (w/v), and
N-acetyl-DL-leucine is administered topically in a concentration ranging from 0.5 to 3% (w/v).

* * * * *